United States Patent [19]

Pettit et al.

[11] Patent Number: 5,569,786

[45] Date of Patent: Oct. 29, 1996

[54] ISOLATION, STRUCTURAL ELUCIDATION AND SYNTHESIS OF NOVEL ANTINEOPLASTIC SUBSTANCES DENOMINATED "COMBRETASTATINS"

[75] Inventors: George R. Pettit, Paradise Valley; Sheo B. Singh, Tempe, both of Ariz.

[73] Assignee: Arizona Board of Regents acting on behalf of Arizona State University, Tempe, Ariz.

[21] Appl. No.: 340,156

[22] Filed: Nov. 15, 1994

Related U.S. Application Data

[63] Continuation of Ser. No. 832,998, Feb. 10, 1992, Pat. No. 5,409,953, which is a continuation of Ser. No. 590, Oct. 26, 1987, abandoned.

[51] Int. Cl.⁶ ............... C07C 43/205; C07D 317/54; A61K 31/09; A61K 31/36
[52] U.S. Cl. ................... 568/646; 568/631; 549/437
[58] Field of Search ............... 568/646, 631; 514/720, 721, 464; 549/437

[56] References Cited

U.S. PATENT DOCUMENTS

| | | | |
|---|---|---|---|
| 2,496,968 | 2/1950 | Walton et al. | 568/646 |
| 3,577,230 | 5/1971 | Sheers | 514/720 |
| 3,968,234 | 7/1976 | Jurd | 424/282 |
| 4,326,055 | 4/1982 | Loeliger | 568/631 |
| 4,482,728 | 11/1984 | Jurd | 549/435 |
| 4,876,270 | 10/1989 | Waespe | 549/437 |
| 4,996,237 | 2/1991 | Pettit et al. | 568/646 |

FOREIGN PATENT DOCUMENTS

| | | |
|---|---|---|
| 0463336 | 2/1950 | Canada. |
| 0276051 | 7/1988 | European Pat. Off.. |
| 0943772 | 12/1963 | United Kingdom. |
| 1046380 | 11/1966 | United Kingdom. |
| 9216486 | 10/1992 | WIPO. |

OTHER PUBLICATIONS

Bachelor et al, "Synthesis of Pinosylvin and Related Heartwood Stibenes", Canadian Journal of Chemistry, vol. 48, No. 10, 1554 (1970).

Primary Examiner—Richard L. Raymond
Assistant Examiner—Deborah Lambkin
Attorney, Agent, or Firm—Richard R. Mybeck

[57] ABSTRACT

New antineoplastic substances have been isolated, structurally elucidated and synthesized having a general structural formula of:

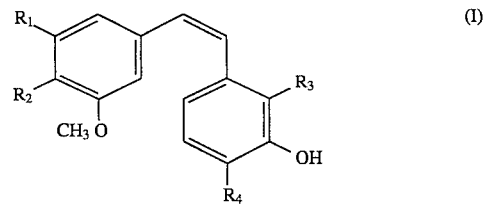

(I)

or

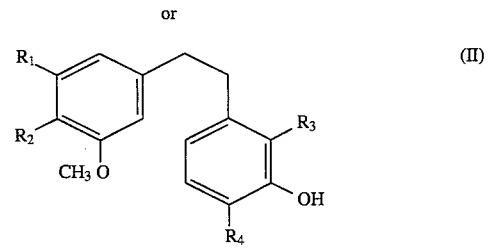

(II)

wherein:

$R_1$ is OH or $OCH_3$;

$R_2$ is H or $OCH_3$; or $R_1R_2$ is $—OCH_2O—$;

$R_3$ is H or OH; and $R_4$ is OH or $OCH_3$.

These substances have been denominated "combretastatin A-1, -A-2, -A-3, -B-1, -B-2, -B-3 and -B-4". preparation containing the substances and methods of treating a host inflicted with a neoplastic growth with the preparation is described.

14 Claims, No Drawings

ISOLATION, STRUCTURAL ELUCIDATION AND SYNTHESIS OF NOVEL ANTINEOPLASTIC SUBSTANCES DENOMINATED "COMBRETASTATINS"

A portion of the work reported herein was funded under Grant CA-30311-01A3 from the National Cancer Institute and Contract No1-CM-97262 of the National Institute of Health.

This invention is a continuation of U.S. patent application Ser. No. 07/832,998 filed Feb. 10 1992, U.S. Pat. No. 5,409,953, for ISOLATION, STRUCTURAL ELUCIDATION AND SYNTHESIS OF NOVEL ANTINEOPLASTIC SUBSTANCES DENOMINATED "COMBRETASTATINS" which was a continuation of U.S. patent application Ser. No. 07/000,590, filed Oct. 26, 1987, now abandoned.

This invention relates to isolation, structural elucidation, and synthesis of new antineoplastic substances herein denominated "combretastatin A-1", "combretastatin A-2", "combretastatin A-3", "combretastatin B-1", "combretastatin B-2", "combretastatin B-3" and "combretastatin B-4", said substances having a general structural formula of:

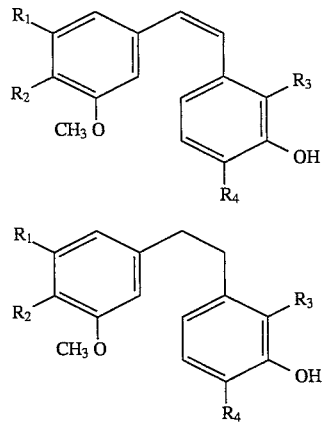

wherein:

$R_1$ is OH or $OCH_3$;

$R_2$ is H or $OCH_3$; or $R_1 R_2$ is $-OCH_2O-$;

$R_3$ is H or OH; and $R_4$ is OH or $OCH_3$.

BACKGROUND OF THE INVENTION

Tropical and subtropical shrubs and trees of the Combretacae family represent a practically unexplored reservoir of new substances with potentially useful biological properties. Illustrative is the genus Combretum with 25 species (10% of the total) known in the primitive medical practices of Africa and India for uses as diverse as treating leprosy (See: Watt, J. M. et al, "The Medicinal and Poisonous Plants of Southern and Eastern Africa" E & S Livingstone, Ltd., London, 1962, p 194) (*Combretum sp.* root) and cancer (*Combretum latifolium*). But only a few species principally *Combretum micranthum* (used in Northern Zimbabwe for mental illness) (See: Ogan, A. U., *Planta Medica*, 1972, 21, 210; and Malcolm, S. A. et al, Lloydia, 1969, 32, 512.) and *C zeyheri* (scorpion envenomation) (See: Mwauluka, K. et al, *Biochem. Physiol. Pflanzen*, 1975, 168, 15) have received any scientific study.

The present investigation was undertaken to determine the murine P388 lymphocytic leukemia (PS system) inhibitory constituents of *Combretum caffrum* (Eckl. and Zeyh) Kuntze (also as *C. Salicifolimum* E. Mey), a potentially useful lead which came out of the U.S. National Cancer Institute's world-wide exploratory survey of plants. In South Africa this tree is known by the Zulu as Mdubu (used as a charm) and is otherwise known as bushveld willow, bushwillow and rooiblaar. The timber is principally used on African farms as scrap wood and fuel. Interestingly, honey arising from the nectar of this tree is strongly bitter but no problems have been recorded from human consumption.

BRIEF SUMMARY OF THE INVENTION

New antineoplastic substances have been isolated, structurally elucidated and synthesized which have a general structural formula of:

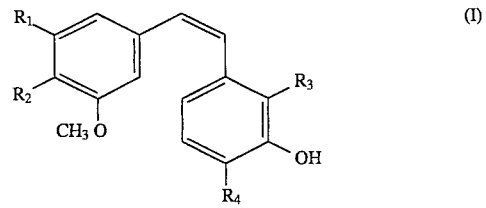

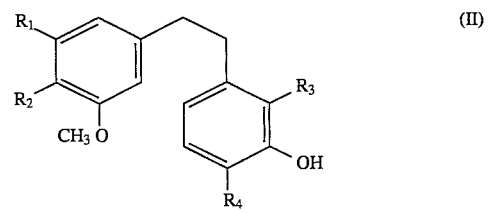

wherein:

$R_1$ is OH or $OCH_3$;

$R_2$ is H or $OCH_3$; or $R_1 R_2$ is $-OCH_2O-$;

$R_3$ is H or OH; and $R_4$ is OH or $OCH_3$.

The substances have been denominated combretastatins A-1, A-2, A-3, B-1, B-2, B-3 and B-4 and are specifically structured as follows, reference being made to the general structures shown above at I and II.

| Combretastatin | Structure | $R_1$ | $R_2$ | $R_3$ | $R_4$ |
|---|---|---|---|---|---|
| A-1 | I | $OCH_3$ | $OCH_3$ | OH | $OCH_3$ |
| A-2 | I | $-OCH_2O$ | $-OCH_2O$ | H | $OCH_3$ |
| A-3 | I | OH | $OCH_3$ | H | $OCH_3$ |
| B-1 | II | $OCH_3$ | $OCH_3$ | OH | $OCH_3$ |
| B-2 | II | OH | $OCH_3$ | H | $OCH_3$ |
| B-3 | II | $OCH_3$ | $OCH_3$ | H | OH |
| B-4 | II | $OCH_3$ | H | H | OH |

The substances are extracted from the stem wood of *Combretum caffrum* with 1:1 methylene chloride and converted to a methylene chloride fraction that was partitioned between hexane and methanol-water followed by adjustment to 3:2 methanol-water and extraction with methylene chloride. The methylene chloride fraction was separated by steric exclusion chromatography on SEPHADEX® LH-20 to obtain the fractions. The isolation of the specific substances from the fraction is detailed in the several examples reported below.

Accordingly, a principle object of the present invention is to isolate and elucidate the structure of new antineoplastic substances from *Combretum caffrum* and to provide the methodology for the efficient and reliable replication thereof by synthetic procedures.

Another object of the present invention is to provide new and useful pharmaceutical preparations containing one of the new antineoplastic substances as the essential active ingredient thereof.

These and still further objects as shall hereinafter appear are fulfilled by the present invention in a remarkably unexpected fashion as will be readily discerned from a careful consideration of the following detailed description of preferred embodiments thereof especially when read in conjunction with the several examples appended thereto.

DESCRIPTION OF THE PREFERRED EMBODIMENT

In the course of the work which culminated in the present invention, we isolated a new substance that caused pronounced astrocyte reversal in the NCI astrocytoma bioassay and was found to be R(−)-1-(3,4,5-tri-methoxy phenyl)-2-(3'-hydroxy,4'-methoxyphenyl)-ethanol. We named this substance "combretastatin". Meanwhile, attention was focused on uncovering the principal PS in vivo active constituent(s) of *Combretum caffrum* fractions where combretastatin was not responsible for the biological activity. The problem was complicated by eventual loss of in vivo activity in fractions obtained from the original large scale extraction of the stems and fruit parts which led to combretastatin. Consequently the large scale (77 kg) extraction of *Combretum caffrum* was repeated using the stem-wood and methylene chloride-methanol as solvent and the efforts resulted in the isolation, structural elucidation and ultimate synthesis of new substances forming the crux of this invention which, as will hereinafter appear, have a general structural formula determined to be either:

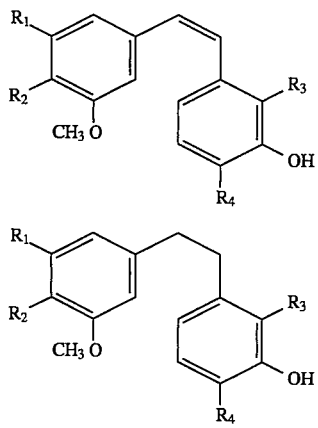

wherein:

$R_1$ is OH or $OCH_3$;

$R_2$ is H or $OCH_3$; or $R_1$ $R_2$ is —$OCH_2O$—;

$R_3$ is H or OH; and $R_4$ is OH or $OCH_3$.

The methylene chloride fraction obtained by diluting the methylene chloride-methanol extract with water was subjected to solvent partition between methanol-water (9:1–3:2) with hexanemethylene chloride. By this means the PS in vivo of activity 38–41% life extension at 25–50 mg/kg and $ED_{50}$ 0.21 µg/mL was concentrated in the methylene chloride fraction. Steric exclusion chromatography of the active methylene chloride fraction in methanol on SEPHADEX LH-20 led to a fraction (30.6 g) preserving the PS in vivo activity. At this stage it was found most effective to proceed by partition chromatography on SEPHADEX LH-20 with 3:1:1 hexane-toluene-methanol as mobil phase. The PS activity (30–48% life extension at 12.5–50 mg/kg) was nicely concentrated in an active fraction that was further purified by SILICA GEL column chromatography and eluted with hexane-ethyl acetate (3:1). After recrystallization of this active component herein named "combretastatin A-1" (0.70 g) obtained in $9.1\times10^{-4}$% yield it was unequivocally assigned the structure shown above as structure I when $R_1=R_2=R_4=OCH_3$ and $R_3$ is OH. (NSC 600032, PS 26–29% increase in life extension at 2.75–11 mg/kg dose levels and $ED_{50}$ 0.99 µg/mL, experiments at higher dose levels are now in progress) and the companion cell growth inhibitory substance was denominated combretastatin B-1 and assigned structure shown as structure II above when $R_1=R_2=R_4=OCH_3$ $R_3$ is OH (PS $ED_{50}$ 1.7 µg/mL, NSC 601291), as follows.

Both the ultraviolet and infrared spectra of combretastatins A-1 and B-1 suggested aromatic systems and this was further supported by the high resolution electron impact mass spectrum and assigned molecular formula $C_{18}H_{20}O_6$ and $C_{18}H_{22}O_6$ respectively. The 400 MHz $^1$H-NMR spectrum exhibited signals for four methoxy group protons and in general indicated that combretastatin B-1 was a dihydro derivative of the A-1. Thus, further structural efforts were concentrated on determining the structure of combretastatin A-1.

The 400 MHz $^1$H-NMR spectrum of combretastatin A-1 exhibited two magnetically identical and relatively shielded aromatic protons at δ6.460, two AB spin systems totalling four aromatic protons with one of these appearing as a doublet at δ6.310 (J=8.64 Hz) and its counterpart at δ6.691 typical of two ortho coupled aromatic protons. The other AB spin system showed doublets at δ6,453 and 6.523 (J=12.2 Hz each). A two-proton signal at δ5.438 was readily exchanged for deuterium upon adding deuterium oxide suggesting the presence of phenolic groups and that observation was confirmed by acetylating.

The mass spectrum of combretastatin B-1 gave a relatively small molecular ion at m/z 334 and two major fragment ions at m/z 181 ($C_{10}H_{13}O_3$) and 153 ($C_8H_9O_3$) resulting from cleavage of the benzyl bond. Results of the mass spectral analysis suggested the presence of three methoxyl groups in one aromatic ring and a methoxy and two hydroxy groups in the other aromatic ring. The relationship to combretastatin A-1 was easily established by selective catalytic hydrogenation of the A-1 to B-1. With the relationship of combretastatin A-1 to B-1 established, examination of the H-NMR spectrum of combretastatin B-1 was very helpful and revealed absence of the two proton doublets at δ6.453 and 6.523. With the relatively large coupling constant and introduction of a 4-proton multiplet at δ2.851 typical of the benzyl protons of a bibenzyl (dihydrostilbene), combretastatin A-1 was assumed to be a stilbene.

Interpretation of the $C^{13}$-NMR spectrum (Table III) of combretastatins A-1 and B-1 suggested each contained a 3,4,5-trimethoxy phenyl ring on the basis of chemical shift additive rules. In the other aromatic ring the position of the two carbons with proton substituents was readily established, but the hydroxy vs. methoxy substituent arrangement was ambiguous. Eventually the substitution pattern in both aromatic rings was established as shown for combretastatin A-1 and B-1 by application of nuclear Overhauser effect difference spectroscopy (NOEDS) methods. The most important observation here resulted from irradiation of the methoxy group at δ3.770 resulting in a 4.3% enhancement of the ring-proton doublet at δ6.310.

The remaining uncertainty in completely assigning the structure of combretastatin A-1 on the basis of spectral evidence resided with the bridging olefin proton coupling constants fall in the range of 6–12 Hz for cis protons and 12–18 Hz for trans protons with 10 and 17 being typical values. While phenolic plant constituents of the stilbene type are generally isolated as the trans-isomers (such as from Eucalyptus species) wood of the emetic *Schotis Brachypetala* Sond (Leguminosae) has been shown to contain a pentahydroxy cis-stilbene. More recently *Rheum rhatonticum* L. (Polygonacae) the commercial rhubarb has been found to contain five cis-stilbenes and fourteen of the trans isomers. In the Rheum stilbene study a comparison of otherwise identical cis- and trans-stilbenes was possible and the cis-olefin proton coupling constants were found to be 12 Hz and the trans 16 Hz. These values correspond well with those later recorded in this investigation as a result of the total synthesis summarized in the sequel. Before this information became available for interpreting significance of the combretastatin A-1 coupling constant at 12.2 Hz the structure was unequivocally established by an x-ray-crystal structure elucidation.

The crystal structure of combretastatin A-1 was solved by direct methods using a SHELX-84 computer technique combined with refinement and difference syntheses based on SHELX-76. The molecular parameters were established using the program PARST and the molecular parameters were established using the program PARST and the molecular representation shown below as FIG. 1 using PLUTO.

Combretastatin A-1 was obtained as plates in the moloclinic crystal system with space group P.2.1c. Bond lengths and angles were found to be the expected order of magnitude. The cis-olefin geometry was confirmed by the torsion angle C(1)-C(1a)-C(1'a)-C(1') at −6(1)°. Normals to the least-squares planes of the two phenyl rings were found inclined at 66.3(2)° to each other and this distortion from an overall planarity of the molecule was further evidenced by the deviation from zero of the three torsion angles C(6')-C(1')-C(1'a)-C(1a) at −16(1)°, C(1') C(1'a)-C(1a)-C(1) at −6(1)° and C(1'a)-C(1a)-C(1)-C(6) at −58(1)°. Most likely this results from the strong steric interaction in a single molecule between C(1) ... C(6') of 3.372(8) A and C(6) .. . C(6') of 3.273(9) A. Close contacts between 0(2') ... 0(4), 3.242(6) A, 0(2') ... 0(5), 2,924(6) A and 0(3') ... 0(3), 3.211(6) A are indicative of an intermolecular hydrogen bonding network. With results of the crystal structure analysis in hand, the spectral analyses were firm including the 2,6% NOE enhancement of the proton at C-6' following irradiation of the C-2 proton: a result consistent with Z-geometry. The stage was then set for total synthesis.

In order to obtain larger quantities of combretastatin A-1 for further biological evaluation an efficient synthesis was devised based on condensing protected aldehyde with the ylide derived from phosphonium salt. The important intermediate benzaldehyde required development of an improved synthesis. A selection of approaches to prepare utilizing other available starting material proved inefficient and instead 2,3,4 trihydroxybenzaldehyde proved to be a most effective starting substance. Reaction of phenol with sodium borate in water was found to selectively form the 2,3-borate ester and this allowed specific methylation of the 4-hydroxyl group by dimethyl-sulfate. Acid hydrolysis of the borate ester afforded dihydroxybenzaldehyde which was more suitably reprotected by conversion to the 2,3-tert-butyldimethylsilyl ether. Because of opinion differences in the earlier literature regarding melting points for benzaldehyde, it seemed necessary to provide some additional evidence for the structure. For this purpose benzaldehyde was acetylated and the resulting diacetate was subjected to NMR irradiation of the methoxy signal at δ3.927 and an NOEDS experiment led to 5.3% enhancement of the C-5 proton doublet at δ6,982 thereby confirming the methoxy group at position 4.

FIG. 1

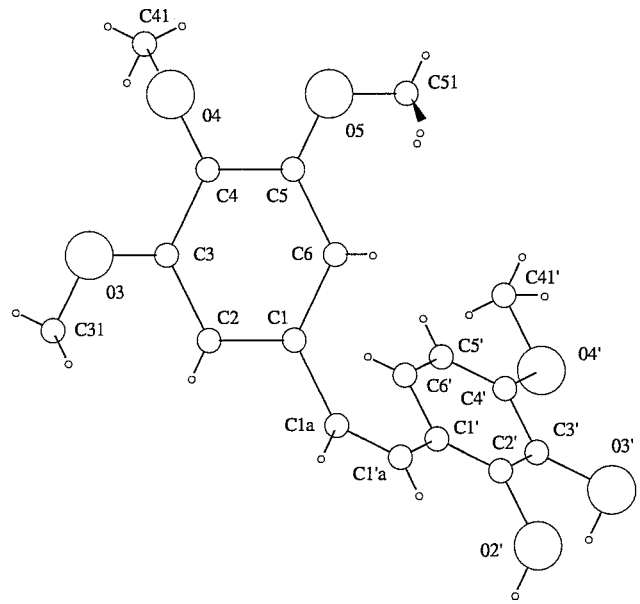

The phosphonium bromide was readily prepared via 3,4, 5-trimethoxybenzyl alcohol and the corresponding ylide (prepared in tetrahydrofuran using butyl lithium) was allowed to react with benzaldehyde. The product was a mixture of olefins and in 92.5% yield with a Z/E ratio of 9:1 by H-NMR analysis. The Z-isomer (75%) was isolated by recrystallization (from ethanol). Complete recovery of the remaining Z-isomer and the E-isomer on a preparative scale, either as the silyl ether derivatives or as the parent phenols, proved difficult but was readily accomplished using the diacetate derivatives. So the mixture of Z/E silyl ethers was treated with tetrabutylammonium fluoride to cleave the silyl protecting groups and the phenols were acetylated and separated by SILICA GEL chromatography to provide combretastatin A-1 diacetate and its trans counterpart diacetate. Cleavage of disilylether with tetrabutyl ammonium fluoride and deacetylation of diacetate with potassium carbonate in methanol afforded combretastatin A-1 identical with the natural product.

The 9:1 Z/E isomer ratio resulting from the Wittig reaction between benzaldehyde and the ylide corresponding to phosphonium bromide requires comment. In the past it appeared that the oxaphosphetanes resulting form reaction of triphenyl-phosphonium alkylids and aldehydes were thermodynamically more stable in the threo configuration when prepared in the presence of lithium salts. The threo oxaphosphetane would then be expected to give predominantly the corresponding trans olefin. In a "salt-free" solution the oxaphosphetane was expected to have the erythro configuration leading to a cis olefin. However, recently Schlosser and Schaub (See: *J. Am. Chem. Soc.*, 1982, 104, 5821) have shown that the stereochemical environment around the group contributed by the ylide is of prime importance. Under "salt-free" conditions using (triethyl-phosphonio)-ethylide in tetrahydrofuran reaction with aldehydes gave high yields of trans olefins. In the Wittig reaction employed to prepare combretastatin A-1 the presence of lithium bromide was obviously unimportant compared to formation of an erythro oxaphosphetane in the most stable configuration. The sterically large silyl protecting groups probably enhance the configuration of erythro over the preferred threo. Since $^1$H-NMR analysis of the crude Wittig reaction product showed a Z/E ratio of 9:1, it appears likely that configuration of the intermediate oxaphosphetane was locked in place by steric effects and that little if any steric "stereochemical drift" occurred between oxaphosphetane formation and production of the cis-olefin. To evaluate the preceding hypothesis the course of the Wittig reaction was studied using $^{31}$P-NMR (61.99 MHz) and the results (cf. experimental) clearly showed that there was no detectable cis-trans interconversion.

Preliminary biological evaluation of olefins 1 and 2 against the PS cell line gave some interesting insights into structural requirements for cell growth inhibitory activity. Combretastatin A-1 diacetate was found to be three-fold less active at PS $ED_{50}$ 2.7 µg/mL than the parent natural product. The trans-isomer counterpart was essentially inactive with PS $ED_{50}$ 12 µg/mL. The silyl ether derivatives were also inactive against the PS cell line. Most importantly combretastatin A-1 was found to have the remarkable property of completely inhibiting microtubulin assembly in vitro at concentrations less than 1.5 µmolar (See Table I). Indeed, combretastatin A-1 appears to be an inhibitor of tubulin polymerization more potent than combretastatin and the well known tubulin inhibitors colchicine and podophyllotoxin.

The newly characterized *Combretum caffrum* natural products Combretastatin A-1 and B-1 were evaluated for in vitro interactions with tubulin (Table I). They were compared to combretastatin and to three additional well-characterized antimitotic agents, namely, colchicine, podophyllotoxin and steganacin, all of which bind at a common site on tubulin.

As appears from Table I, Combretastatin A-1 was more active than combretastatin B-1 in its interactions with tubulin which agrees with its greater antineoplastic activity. Both compounds were significantly more potent that the previously described combretastatin. In microtubule assembly (Table I, Experiment I; see also Example 20 hereof), equivalent inhibition was observed with 2 µM combretastatin A-1, 3 µM combretastatin B-1, and 11 µM combretastatin. The inhibition of assembly with combretastatins A-1 and B-1 was comparable to that observed with podophyllotoxin and greater that observed with colchicine and steganacin.

Combretastatin, podophyllotoxin, steganacin and colchicine all appear to bind at the same site on tubulin, as the first three agents act as competitive inhibitors of the binding of radiolabeled colchicine to the protein. Combretastatins A-1 and B-1 were particularly potent as inhibitors of the binding of (H)colchicine to tubulin (Table I, Experiment II), significantly exceeding the inhibition observed with steganacin, combretastatin and even, in the case of combretastatin A-1, podophyllotoxin.

TABLE I

INHIBITION OF MICROTUBULE ASSEMBLY AND BINDING OF COLCHICINE TO TUBULIN BY COMBRETASTATIN A-1 AND COMBRETASTATIN B-1

| DRUG | EXPERIMENT I $ID_{50}$* (µM) | EXPERIMENT II % of control |
|---|---|---|
| Combretastatin A-1 | 2 | 2.2 |

| DRUG | EXPERIMENT 1 MICROTUBULE ASSEMBLY $ID_{50}$* (µM) | EXPERIMENT II COLCHICINE BINDING % of control |
|---|---|---|
| Combretastatin B-1 | 3 | 13 |
| Combretastatin | 11 | 34 |
| Podophyllotoxin | 3 | 13 |
| Steganacin | 6 | 49 |
| Colchicine | 6 | — |

*Defined as the drug concentration inhibiting the extent of microtubule assembly by 50%.

EXPERIMENTAL SECTION

Synthetic intermediates were employed as received from Sigma-Aldrich. Solvents used for chromatographic procedures were redistilled. The SEPHADEX LH-20 (particle size 25–100 µm) used for steric exclusion chromatography was obtained from Pharmacia Fine Chemicals AB (Uppsala, Sweden). SILICA GEL 60 (40–230 mesh) utilized for column adsorption chromatography and the LOBAR SILICA GEL 60 columns (size B) were supplied by E. Merck (Darmstadt, Germany). Silica gel GHLF Uniplates (0.25 mm layer thickness) were obtained from Analtech, Inc., (Newark, Del.) the TL chromatograms were developed with anisaldehyde-acetic acid or ceric sulfate-sulfuric acid spray reagents (by heating at approximately 150° C. for 5–10 min) or by application of ultraviolet light.

While the experimental procedures described above are directed to the preparation of combretastatin A-1 and its conversion to combretastatin B-1, it should be realized that the approach described is equally applicable to the preparation of those combretastatins denominated A-2, A-3, and B-2, B-3 and B-4 as will become more apparent from a careful consideration of the Examples set forth below.

Thus, in each of the synthetic procedures, solvent extracts of aqueous solutions were dried over anhydrous sodium sulfate. Ether refers to diethyl ether. Each pure specimen was colorless. The mutual identity of natural and synthetic specimens was established by comparison of infra red (NaCl) plates and H-NMR spectra combined with results from thin layer chromatographic (TLC) comparisons in several solvents. All melting points are uncorrected and were observed with a Kofler-type hot-stage apparatus. Ultraviolet spectra were obtained and recorded using a HEWLETT-PACKARD model 8540AUV/VIS spectrophotometer. Infra red spectra were measure with a NICKOLET FT-IR model MX-1 unit. Nuclear magnetic resonance spectra were obtained with a BRUKER WH-90 and AM-400 instrument with deuteriochloroform as solvent and tetramethyl-silane as the internal standard. The chemical shifts were recorded using the δ scale. The SFORD technique was used for determining multiplicities in C-NMR spectra. Nuclear Overhauser effect difference spectroscopy (NOEDS) experiments were performed with a deuteriochloroform solution degassed six times by the freeze-thaw technique. Mass spectral determinations were made with a MS-50 instrument at the NSF Regional Facility, University of Nebraska, Lincoln, Neb. Elemental microanalyses were performed at Mic-Anal, Tucson, Ariz. The X-ray crystal structure determination was performed with an ENRAF-NONIUM CAD-4 diffractometer and all computations were performed using a SPERRY 1100 computer.

Isolation of Combretastatin A-2, A-3, and B-2

The stem wood (77 kg dry wt.) of *Combretum caffrum* was extracted with 1:1 methylene chloride and converted to a methylene chloride fraction that was partitioned between hexane and methanol-water (9:1) followed by adjustment to 3:2 methanol-water and extraction with methylene chloride. The methylene chloride fraction (827.99 g) from the solvent partitioning sequence was separated by steric exclusion chromatography on SEPHADEX LH-20 to obtain fractions A and B.

Fraction A (28.6 g) was further separated on a column of SEPHADEX LH-20 (2.5 kg) by partition chromatography employing hexane-toluene-methanol (3:1:1) to furnish an active fraction (2.07 G, PS $ED_{50}$ $1.8 \times 10^{-2}$ μ/ml) which was dissolved in hexaneethyl acetate (1:1, 5 ml) and chromatographed on a column (60×2.5 cm) of SILICA GEL (60 g). Gradient elution from 4:1→1:1 hexane-ethyl acetate afforded in a 3:1 fraction the next PS (0.7 g, $ED_{50}$ $1.0 \times 10^{-2}$ μg/ml) active material. Rechromatography in acetone (2 ml) over a long column (100×1.2 cm) of SILICA GEL (45 g) using the gradient hexane-ethyl acetate 9:1→4:1 yielded in a 4:1 fraction a pure specimen of combretastatin A-2 (0.442 g, $5.74 \times 10^{-4}$% base on the dried plant, PS $ED_{50}$ $2.7 \times 10^{-2}$ μg/ml as a viscous oil: Rf. 0.46 (1:1 hexane-ethyl acetate), UV ($CH_3OH$) λmax(ε) 223 (17175), 303 (7190); IR ν (NaCl) 3490, 1508, 1452, 1440, 1427, 1272, 1196, 1129, 1114, 1085, 1042, 930 cm$^{-1}$; $^1$H-NMR (400 MHz) 3.750 (3H, s, $OCH_3$), 3.870 (3H, s, $OCH_3$), 5.520 (1H, s, OH, disappeared upon adding $D_2O$, 5.935 (2H, s, —$OCH_2O$—), 6.383 (1H, d, J=12.16 Hz, —CH=CH—) 6.420 (1H, d, J=12.16 Hz, —CH=CH—), d, J=12.16 Hz, —CH=CH—), 6.458 (1H, d, J=1.32 Hz, H-2 or H-6), 6.483 (1H, d, J=1.32 Hz, H-6 or H-2), 6.731 (1H, d, J=8.4 Hz, H-5'), 6.773 (1H, dd J=8.4, 2.0 Hz, H-6'), 6.875 (1H, d, J=2.0 Hz, H-2'); $^{13}$C-NMR (see Table II) and HREIMS (M/Z) 300.1001 (100, m, calcd for $C_{17}H_{16}O_5$, 300.0998), 285.0767 (4, $C_{16}H_{13}O_5$), 267.0666 (10, $C_{16}H_{11}O_4$), 239.0714 (17, $C_{15}H_{11}O_3$).

Active fractions B (30.6 g) was also separated in hexane-toluene-methanol (3:1:1) by partition chromatography on SEPHADEX LH-20 (2.5 kg). The PS active components were concentrated in two fractions: 8.11 g (PS, $ED_{50}$ 2.7 μg/ml) and 1.57 g (PS, $ED_{50}$ 0.36 μg/ml). The latter fraction (1.57 g) was chromatographed on a column (70×2.5 cm) of SILICA GEL (70 g) and eluted with hexane-ethyl acetate (4:1→1:1). A fraction eluted with 4:1 hexane-ethyl acetate gave a pure specimen of combretastatin A-3 (480.7 mg, $6.24 \times 10^{-4}$% yield, PS $ED_{50}$ $2.6 \times 10^{-2}$ μg/ml) as a viscous oil: Rf. 0.40 (1:1, hexane-ethyl acetate) UV ($CH_3OH$ $λ_{max}$ (ε) 251(8090), 295(8895). UV($CH_3OH+NaOCH_3$) $λ_{max}$ 259 (9078, 279 (7383)), 296 (7402); IR $λ_{max}$ (NaCl) 3430, 1583, 1509, 1458, 1441, 1430, 1274, 1234, 1201, 1114, 1104 cm$^{-1}$; $^1$H-NMR (400 MHz) 3.668 (3H, s, $OCH_3$), 3.867 (3H, s, $OCH_3$), 3.886 (3H, s, $OCH_3$), 5.154, 5.680 (1H, each, brs, OH, $D_2O$ exchanged), 6.381 (1H, d, J=12.2 Hz, —CH=CH—), 6.427 (1H, d, J=1.72 Hz, H-6) 6.439 (1H, d, J=12.2 Hz, —CH=CH—), 6.535 (1H, d, J=1.72 Hz, H-2), 6.72 (1H, d, J=8.4 Hz, H-5'), 6.792 (1H, dd, J=8.4 Hz, 2.0 Hz, H-6'), 6.897 1H, d, J=2.0 Hz H-2'), $^1$C-NMR (refers to Table II); and HREIMS (m/z 302.1156 (100, M, calcd for $C_{17}H_{18}O_5$: 302.1154), 287.0919 (14, $C_{16}H_{15}O_5$), 269.0813 (14, $C_{16}H_{13}O_4$).

The active fraction weighing 8.11 g was chromatographed in ethyl acetate (20 ml) on a column of SILICA GEL (200 g). Elution with hexane-ethyl acetate (3:1) and combination of earlier fractions furnished a 0.181 g fraction (PS, $ED_{50}$ 0.19 μg/ml) that was further purified on a WHATMANN HPLC column (500×10 mm) packed with PARTISIL (M-9). Elution with hexane-2-proponal (9:1) at a flow rate of 0.56 ml/min afforded pure combretastatin B-2 (51.7 mg, $6.71 \times 10^{-5}$% yield, PS, $ED_{50}$ 0.32 μg/ml as another viscous oil: Rf. 0.42 (1:1 hexane-ethyl acetate); UV ($CH_3OH$) $λ_{max}$ (ε) 220 (22902), 280 (6120); IR $λ_{max}$ (NaCl) 3437, 1595, 1512, 1461, 1442, 1430, 1351, 1278, 1237, 1150 cm$^{-1}$; $^1$H-NMR (400 MHz) 2.785 (1H, brs, —$CH_2$—$CH_2$—), 3.819 (3H, s, $OCH_3$), 3.856 (3H, s, $OCH_3$), 5.605, 5.748 (1H each, brs, OH, $D_2O$ exchanged), 6.264 (1H, d, J=1.88 Hz, H-6), 6.465 (1H, d, J=1.88 Hz, H-2, J=1.88 Hz, H-2), 6.648 (1H, dd, J=8.12, 2.0 Hz, H-6'), 6.760 (1H, d, J=8.12 Hz, H-5'), 6.794 (1H, d, J=2.0 Hz H-2'); $^{13}$C-NMR (see table 1); and HREIMS (M/z); 304.1326 (30, M, calcd for $C_{17}H_{20}O_5$, 304.1311), 167.0708 (100, $C_9H_{11}O_3$), 137.0604 (65, $C_8H_9O_2$).

Isolation of Combretastins B-3 and B-4

The *Combretum caffrum* fraction reported earlier to contain combretastatin A-1 was submitted to further separation on a PARTISIL M-9 column by HPLC with 9:1 hexane-2-propanol as solvent at a flow rate of 1 ml/min to furnish 12.0 mg of combretastatin B-3 as a powder from ethanol-ether, mp 113°–15° C.: PS $ED_{50}$ 0.4 μg/ml; UV ($CH_3OH$) $λ_{max}$ 241 (ε 8450), 281 (6907); UV ($CH_3OH+NaOCH_3$) $ε_{max}$ 246 (10190), 293 (5699); IR $λ_{max}$ 3400, 1590, 1507, 1457, 1420, 1240, 1126 cm$^{-1}$; $^1$H-NMR (400 MHz), 2,796 (4H, s, —$CH_2$— $CH_2$—), 3,871 (6H, s, 2×$OCH_3$), 3.829 (3H, s, $OCH_3$ ), 5,240, 5,350 (1H, each, brs, OH, $D_2O$ exchangeable), 6,307 (1H, dd, J=2.0 Hz each, H-4), 6,322 (2H, brd, J=2.0 Hz, H-2, 6), 6,608 (1H, brd, J=7.8 Hz, H-6'), 6,687 (1H, brs, H-2'), 6,755 (1 H, d, J=7.8 Hz, H-5'); $^1$C-NMR (refer to Table II); and HREIMS (m/z) 274.1208 (M$^+$, 34.5%, calcd for $C_{16}H_{18}O_4$: 274.1205) 152.0822 (29, calcd for $C_9H_{12}O_2$: 152.0837), 151.0746 (15, calcd for $C_9H_{11}O_2$: 151.0759), 123.0450 (100, calcd for $C_7H_7O_2$: 123.0446).

In final separation of the combretastatins, the bibenzyl (3'-hydroxy-3,4,5-trimethoxy bibenzyl) was isolated and recrystallized from acetone-hexane to afford small needles melting at 108° C.: PS $ED_{50}$ 1.7 μg/ml; UV ($CH_3OH$) $λ_{max}$ 222 (25412), 280 (6854); IR $ν_{max}$ 3485, 1609, 1595, 1511, 1469, 1452, 1425, 1207, 1146 cm$^{-1}$; $^1$H-NMR (90 MHz) 2.82 (4H, s, —$CH_2$—$CH_2$—), 3.77 (6H, S, 2×$OCH_3$), 3.86 (3H, s, $OCH_3$), 5.57 (1H, brs, OH, $D_2O$ exchangeable), 6.33 (3H, brs, H-2, 4, 6), 6.64 (1H, dd, J=8.14, 1.8 Hz, H-6'), 6.77 (1H, d, J=8.14 Hz, H-5') 6.80 (1H, d, J=1.8 Hz, H-2'); and HREIMS (m/z) 288.1364 (M, 22%, calcd for $C_{17}H_{20}O_4$: 288.1362), 151.0759), 137.0603 (100, calcd for $C_8H_9O_2$: 137.0603.

The original fraction bearing 2-hydroxy-3,4,6,7-tetramethoxy- 9,10-dihydrophenanthrene was chromatographed on a column of SILICA GEL in 3:1 hexane-ethyl acetate to isolate the bibenzyl (4'-hydroxy-3,5-trimethoxy bibenzyl) (1.15 g) as a viscous oil; UV ($CH_3OH$) $\lambda_{max}$ 236 ($\epsilon$ 3555), 280 (3212), UV ($CH_3OH+NaOCH_3$) $\lambda_{max}$ 247 (6433), 280 (2506), 294 (1795); IR v 3417, 1607, 1596, 1514, 1461, 1429, 1204, 1150, 1066, 850, 690 cm$^{-1}$; $^1$H-NMR (90 MHz) 2.85 (4H, s, —$CH_2$—$CH_2$—), 3.76 (6H, s, 2×$OCH_3$), 5.15 (1H, brs, OH, $D_2O$ exchangeable), 6.32 (3H, s, H-2, 4,6), 6.74 (2H, d, J=8.4 Hz, H-3', 5'), 7.05 (2H, d, J=8.4 Hz, H-2', 6'), no aromatic solvent shift was observed when the spectrum was obtained in a mixture of $C_6D_6$-$CDCl_3$; and HREIMS (m/z 258. 1255 (M, 25%, calcd for $C_{16}H_{18}O_3$: 258.1256), 152.0831 (33, calcd for $C_{912}O_2$: 152.0837), 107.0495 (100, calcd for $C_7H_7O$: 107.0497.

A companion fraction from isolation of the combretastatin B-2 was rechromatographed in 4:1 hexane-ethyl acetate on a column of SILICA GEL, one of the fractions thereby prepared was used for final separation in 9:1 hexane-2-propanol by HPLC on a column of PARTISIL M-9 with a flow rate of 1 ml/min. The result was 10 mg of bibenzyl (4'-hydroxy-3,4,5-trimethoxy bibenzyl) that recrystallized as needles from acetone-hexane; mp 110–12; PS $ED_{50}$ 0.25 µg/ml; IR $\lambda_{max}$ 3411, 1612, 1591, 1514, 1457, 1420, 1328, 1236, 1125, 1098, 840, 750 cm$^{-1}$; $^1$H-NMR (90 MHz) 2.82 (4H, s, —$CH_2$— $CH_2$—), 3.82 (9H, s, 3×$OCH_3$), 4.99 (1H, brs, OH, $D_2O$ exchangeable), 6.35 (2H, s, H-2, 6), 6.75 (2H, d, J=8.6 Hz, H-3', 5'), 7.04 (2H, d, J=8.6 Hz, H-2', 6'); and HREIMS (m/z) 288.136 (M+, 17% calcd for $C_{17}H_{20}O_4$: 288.1362), 181.0863 (100, calcd for $C_{10}H_{13}O_3$: 181.0865), 107.0499 (100, calcd for $C_7H_7O$: 107.0497).

TABLE II

COMBRETASTATIN A-2, A-3, B-2, B-3, AND B4, 13C-NMR (100.6 MHZ) - CHEMICAL SHIFTS ($\delta$) ASSIGNMENTS RELATIVE TO TETRAMETHYLSILANE IN DEUTRIOCHLOROFORM

| Carbon | A-2 | A-3 | B-2 | B-3 | B-4 |
|---|---|---|---|---|---|
| 1 | 131.83 | 133.33 | 138.80 | 137.62 | 144.24 |
| 2 | 108.57 | 108.92 | 108.05 | 105.63 | 106.73 |
| 3 | 143.40 | 145.87$^a$ | 145.61$^a$ | 153.08 | 160.77 |
| 4 | 134.40 | 138.79 | 133.92 | 134.86 | 98.10 |
| 5 | 148.40 | 151.98 | 152.20 | 153.08 | 160.77 |
| 6 | 103.04 | 105.06 | 104.67 | 105.63 | 106.77 |
| 1a | 129.23 | 129.59 | 37.14 | 38.42 | 138.26 |
| 1a' | 128.88 | 128.96 | 38.07 | 37.23 | 36.89 |
| 1' | 130.66 | 130.66 | 135.23 | 134.86 | 135.02 |
| 2' | 115.03 | 115.16 | 114.81 | 115.32 | 115.41* |
| 3' | 145.80$^a$ | 145.25$^a$ | 144.98$^a$ | 141.70 | 141.65** |
| 4' | 145.32$^a$ | 149.05 | 149.16 | 143.53 | 143.48** |
| 5' | 110.45 | 110.45 | 110.82 | 115.70 | 115.71* |
| 6' | 121.04 | 121.14 | 119.82 | 120.92 | 120.91 |

A-2: 101.35 ($OCH_2O$), 56.38, 55.92 ($OCH_3$).
A-3: 60.99 ($OCH_3$ at C-4), 55.92, 55.70 ($OCH_3$).
B-2: 60.97 ($OCH_3$ at C-4), 56.90, 55.90 ($OCH_3$).
B-3: 56.15 ($OCH_3$), 60.94 ($OCH_3$).
B-4: 55.31 ($OCH_3$)
a, *, ** in vertical column may be interchanged The administration of the several combretastatins herein disclosed and their pharmacologically active physiologically compatible derivatives is useful for treating animals or humans having a neoplastic disease, for example, acute lymphocytic leukemia and the like using the accepted protocols of the National Cancer Institute.

The dosage administered will be dependent upon the identity of the neoplastic disease; the type of host involved, including its age, health and weight; the kind of concurrent treatment, if any; and the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The power mixture is prepared by mixing an active ingredient, suitably comminuted, with a diluent or base such as starch, lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions, the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The combretastatin active ingredients to be employed as antineoplastic agents can be easily prepared in such unit dosage form with the employment of pharmaceutical materials which themselves are available in the art and can be prepared by established procedures. Illustrative of the preparation of the unit dosage forms, and not as a limitation thereof, are set forth in Example 43, supra.

To further assist in the understanding of the present invention the following examples are presented to more clearly disclose the present invention and not by way of limitation.

EXAMPLE 1

Plant Taxonomy

Stem wood of the South African tree *Combretum caffrum* (Eckl. and Zeyh) Kuntze was collected and identified as part of the National Cancer Institute—U.S. Department of Agriculture research program directed by Drs. John D. Douros, Matthew I. Suffness and James A. Duke. The stem wood (B817373) employed in this study was obtained in 1979.

EXAMPLE 2

Extraction and Solvent Partition Procedures

The dry stem wood (77 kg) of *Combretum caffrum* was subdivided by chipping and extracted with 1:1 methylene chloride-methanol (320 liters) at ambient temperature for eleven days. The methylene chloride phase was separated by addition of water (25% by volume) and the plant extraction was repeated with another 320 liters of methylene chloride-methanol 1:1 as just described. The combined methylene chloride phases were concentrated to a crude extract weighing 1.42 kg and showing PS in vivo life extension of 27% at 100 mg/kg and PS $ED_{50}$ 5.1 µg/mL. A solution of the methylene chloride fraction was partitioned 5× between hexane (18 liters) and methanol-water (9:1, 18 liters). After separating the hexane phase, the methanol-water was adjusted to a concentration of 3:2 and extracted (5×) with methylene chloride (18 liters). The hexane extract (602.3 g) proved PS in vivo inactive and marginally active against the cell line with $ED_{50}$ 2.4 µg/mL. The PS in vivo activity (38–41% life extension at 25–50 mg/kg) and major cell growth inhibition ($ED_{50}$ 0.21 µg/mL) was concentrated in the methylene chloride fraction (827.9 g) from the solvent partitioning sequence.

EXAMPLE 3

Isolation of Combretastatin A-1

The methylene chloride fraction from the solvent partitioning sequence was dissolved in methanol (7×500 mL) and further separated by steric exclusion chromatography on columns of SEPHADEX LH-20 (7×2.5 kg). The PS active (41% life extension at 12.5 mg/kg and $ED_{50}$ 0.18 µg/mL fraction (30.6 g) was further separated in hexane-toluene-methanol (3:1:1) solution by partition chromatography on SEPHADEX LH-20 (2.5 kg). Further concentration of the active components was achieved by this important separation step that gave a fraction (8.11 g) with 30–40% life extension at 12.5+50 mg/kg and $ED_{50}$ 2.7 µg/mL in the bioassay. The 8.11 g active fraction was chromatographed in ethyl acetate (20 mL) on a column of SILICA GEL (200 g). Elution with hexane-ethyl acetate (3:1) led to two active fractions weighing 0.64 g and 2.25 g. Recrystallization of the 2.25 g fraction from hexane-chloroform afforded a pure specimen of combretastatin A-1 (0.70 g, $9.1\times10^{-4}$% yield based on the dried plant) as plates melting at 113°–15° C.:

UV (CH$_3$OH) $\lambda_{max}$ 233, 255, 298 mµ ($\epsilon$ 7145, 7766, 7848); UV (CH$_3$OH+CH$_3$ONa) $\lambda_{max}$ 232, 255, 288, 397 mµ ($\epsilon$ 7323, 7679, 7038, 1983); IR (film) 3482, 3426, 1580, 1507, 1480, 1463, 1452, 1328, 1290, 1238, 1125, 1092, 1000, 915, 850 cm$^{-1}$; $^1$H-NMR (400 MHz) 3.597 (6H, s, 2×OCH$_3$ —3, 5), 3.760 (3H, s, OCH$_3$ —4), 3,770 (3H, s, OCH$_3$ 4'), 5.438 (2H, brs, disappeared upon D$_2$O exchange 2XOH—2' 3' 6 310 (1H, d, J$_{AB}$=8.64 Hz, H-5'), 6,453 (1H, d, J$_{A'B}$=12.2 HZ, —CH═CH—), 6.460 (2h, S, h-2,6), 6,523 (1h, D, J$_{B'A}$=12.2 HZ, —CH═CH—), 6.691 (1H, d, J$_{BA}$=8.6 HZ, H-6'); C-NMR (see Table III); and HREIMS (m/z) 332.1248 (M$^+$, 100%, calcd 332.1259 for C$_{18}$H$_{20}$O$_6$) and 317.1005 (M-CH3, 93.7%, C$_{17}$H$_{17}$O$_6$). Anal. Calcd for C$_{18}$H$_{20}$O$_6$: C, 65.05; H, 6.06. Found C, 64.80; H, 6.08.

EXAMPLE 4

Isolation of Combretastatin B-1

The 0.6 active fraction from the SILICA GEL column chromatograph produced by Example 3 was rechromatographed using two LOBAR B columns in series. Elution with hexane-ethyl acetate (7:3) provided combretastatin B-1 as an oil (39.6 mg) in 5.1×10$^{-5}$% yield based on the dry plant starting material. The colorless gummy combretastatin B-1 (3) exhibited UV (CH$_3$OH) $\lambda_{max}$ 239, 270 mµ ($\epsilon$ 5845, 1949); UV (CH$_3$OH+CH$_3$ONa) $\lambda_{max}$ 240, 256 mµ ($\epsilon$ 5860, 5949); IR (film) 3424, 3408, 1590, 1508, 1457, 1288, 1126, 1093 cm$^{-1}$; $^1$H═NMR (400 MHz) 2.851 (4H, m, —CH$_2$—CH$_2$—), 3.827 (3H, s, OCH$_3$–4'), 3,831 (6H, s, 2×OCH$_3$ –3, 5), 3,856 (3H, s, OCH$_3$ —4), 5.382, 8.398 (1H each, D$_2$O exchangeable, 2×OH—2',3'), 6.390 (1H, d, J$_{AB}$=8.36 HZ, H-5'), 6,420 (2H, s, H-2,6), 6.577 (1H, d, J$_{BA}$=8.36 HZ, H-6'); C-NMR (refer to Table III); and HREIMS (m/z), 334.1417 (27.2%, M, calcd, C$_{18}$H$_{22}$O$_6$ for 334, 1416, 181.0861 (100, calcd C$_{10}$H$_{13}$O$_3$ for 181.0865) and 153.0549 (59.6 calcd C$_8$H$_9$O$_3$ for 153.0552).

TABLE III

Combretastatin A-1 and B-1 $^{13}$C-NMR (100 MHz) Chemical Shift Assignments relative to Tetramethylsilane in Deuteriochloroform Solution

| Structure Assign. No. | A-1 | B-1 |
| --- | --- | --- |
| 1 | 132049* | 138.18 |
| 2 | 106.13 | 105.67 |
| 3 | 152.80 | 153.05 |
| 4 | 132.67* | 132.35 |
| 5 | 152.80 | 153.05 |
| 6 | 106.13 | 105.67 |
| 1a | 130.21** | 36.46** |
| 1'a | 124.06** | 31.82** |
| 1' | 117.91 | 121.55 |
| 2' | 141.72 | 142.19 |
| 3' | 137.42 | 136.21 |
| 4' | 146.37 | 145.40 |
| 5' | 102.98 | 102.52 |
| 6' | 120.17 | 120.32 |
| 3,5-OCH$_3$ | 55.85 | 56.12 |
| 4-OCH$_3$ | 60.79 | 60.18 |
| 4'-OCH$_3$ | 56.16 | 56.18 |

*, ** Assignments may be interchanged.

EXAMPLE 5

Acetylation of Combretastatin A-1

A solution of combretastatin A-1 (5 mg) in 0.5 mL of 1:1 acetic anhydride-pyridine was allowed to stand overnight at room temperature. The volatile components were evaporated under a stream of nitrogen and the product crystallized from hexane-ethyl acetate to afford colorless plates of the acetate: mp 133°–35°; IR (film) 1775, 1579, 1503, 1454, 1420, 1206, 1174, 1127, 1088, 1010 cm$^{-1}$; $^1$H-NMR (400 MHz) 2.264, 2.99 (3H each, s, COCH$_3$), 3.664 (6H, s, 2×OCH$_3$), 3.807 (3H, s, OCH$_3$) 3.813 (3H, s, OCH$_3$), 6.361 (1H, d, J$_{AB}$=11.90 HZ, —CH═CH—), 6.442 (2H, S, H-2,6), 6.548 (1H, d, J$_{BA}$=11.90 HZ, —CH═CH—), 6.726 (1H, d, J$_{A'B}$=8.7 HZ, H-5'), 7.025 1H, d, J$_{B'A}$=8.7 HZ, H-6'); and HREIMS (m/z) 416.1463 (60M, calcd C$_{22}$H$_{24}$O$_8$ for 416.1471), 374.1363 (70.M+H)$^+$ —COCH$_3$, C$_{20}$H$_{22}$O$_7$), and 332.1263 (100, (M+2H)$^+$ —2×COCH$_3$, C$_{18}$H$_{18}$ O$_6$).

EXAMPLE 6

A mixture of combretastatin A-1 (35 mg) in methanol (15 mL) and 5% Pd/C (10 mg) was treated with a positive pressure of hydrogen at ambient temperature overnight. Catalyst was removed by filtering the yellow solution and the product was purified by preparative layer chromatography by WHATMAN KC18 plates with acetone-methylene chloride (1:11.5) as mobile phase. The product was identical (by TLC, IR and NMR) with natural combretastatin B-1.

EXAMPLE 7

The Crystal and Molecular Structure of Combretastatin A-1

Single crystals of combretastatin A-1 were obtained from hexane-chloroform. The crystals were small very thin plates and as such not entirely suitable for X-ray irradiation. During the data collection, intensities of three standard reference reflections monitored every hour and centering checked every hundred measured relections. Intensities were corrected for Lorentz and polarization effects but not for absorption. The structure was solved by direct methods using a preliminary version of SHELX-84 which yielded in an E map, 23 of the 24 non-hydrogen atoms. Subsequent refinement and difference syntheses using SHELX-76 enabled location of the remaining non-hydrogen atom. Hydrogen atoms of the phenyl rings and the olefinic group were placed in calculated positions with a single temperature factor. Methyl hydrogens were treated as rigid groups with a single temperature factor. The two hydroxyl hydrogens were initially placed as located in a difference map and constrained to ride at 1.00 Å from their parent oxygens. In the final refinements all atoms were treated with isotropic thermal motion. Molecular parameters were obtained using PARST (See: Nardelli, M., Comput Chem 1983, 7, 95) and a drawing of the molecule using PLUTO (See: Motherwell, W. D. S., Pluto Plotting Program, Cambridge University, England, 1974, unpublished). Further details of the data collection solution and refinement of the structure are shown in Table IV, below. Final atomic coordinates of the molecule are shown in Table IV, below. Final atomic coordinates of the molecule are shown in Table V, below, and a perspective view with atomic nomenclature is shown at FIG. 1, above. Relevant molecular parameters are reported in Table VI below.

TABLE IV

Crystallographic Data and Summary of Intensity Data Collection and Structure Refinement for Combretastatin A-1

| | |
| --- | --- |
| Molecular formula | C$_{18}$H$_{20}$O$_6$ |
| Mr. g mol | 332.35 |

TABLE IV-continued

Crystallographic Data and Summary of Intensity Data Collection and Structure Refinement for Combretastatin A-1

| | |
|---|---|
| Crystal system | monoclinic |
| Space group | P2₁/c |
| T, K | 294 |
| a, Å | 10.497 (2) |
| b, Å | 6.717 (2) |
| c, Å | 22.746 (4) |
| β, ° | 96.11 (2) |
| V, Å³ | 1594.7 (6) |
| Z | 4 |
| d calc, g cm⁻³ | 1.38 |
| Crystal dimensions, mm | 0.06 × 0.16 × 0.34 |
| Radiation wavelength MoK a, Å | 0.7107 |
| Crystal decay, % | 1 |
| μ, cm⁻¹ | 0.972 |
| F (000) | 704 |
| Scan Mode | ω-2 Θ |
| Scan width in ω, ° | (0.64 + 0.35 tan O) |
| Aperture width, mm | (1.12 + 1.05 tan O) |
| Aperture length, mm | 4 |
| Final acceptance limit | 20τ at 20° min |
| Maximum recording time, s | 40 |
| Scan range, 2Θ | 2–46 |
| No. of reflections collected | 1793 |
| No. of reflections observed (with $I_{rel} > 2 \sigma I_{rel}$) | 1265 |
| No. of parameters | 0.076 |
| $R = \Sigma \| Fo \|-\| Fe \|/\Sigma \|Fo\|$ | 0.74 |
| $Rw = \Sigma w^{1/2} \|Fo\|-\|Fe\|/\Sigma w^{1/2} \|Fo\|(\sigma^2 F) - 1$ | |

TABLE V

Fractional atomic coordinates (× 10⁴) and temperature factors (Å² × 10³) for non-hydrogen atoms of combretastatins A-1

| | x/a | y/b | z/c | Uiso |
|---|---|---|---|---|
| C(1) | 6517(6) | 4976(9) | 1646(3) | 37(2) |
| C(2) | 6985(6) | 6387(10) | 1286(3) | 36(2) |
| C(3) | 8212(6) | 6159(9) | 1116(3) | 37(2) |
| O(3) | 8750(4) | 7487(7) | 742(2) | 50(1) |
| C(31) | 7995(7) | 9107(10) | 512(3) | 52(2) |
| C(4) | 8988(6) | 4633(9) | 1319(3) | 32(2) |
| O(4) | 10241(4) | 4564(6) | 1183(2) | 42(1) |
| C(41) | 10442(7) | 3270(11) | 711(3) | 57(2) |
| C(5) | 8514(6) | 3209(9) | 1675(3) | 33(2) |
| O(5) | 9352(4) | 1693(6) | 1862(2) | 39(1) |
| C(51) | 8917(6) | 157(10) | 2230(3) | 42(2) |
| C(6) | 7286(5) | 3361(10) | 1845(3) | 34(2) |
| C(1a) | 5250(6) | 5280(10) | 1852(3) | 42(2) |
| C(1'a) | 4222(6) | 4122(9) | 1822(3) | 38(2) |
| C(1') | 3959(5) | 2190(9) | 1519(3) | 34(2) |
| C(2') | 2868(5) | 1124(9) | 1638(3) | 34(2) |
| O(2') | 2148(4) | 1839(7) | 2063(2) | 45(1) |
| C(3') | 2509(6) | −621(9) | 1350(3) | 34(2) |
| O(3') | 1431(4) | −1586(7) | 1510(2) | 21(1) |
| C(4') | 3198(5) | −1314(9) | 916(3) | 32(2) |
| O(4') | 2702(4) | −3024(7) | 635(2) | 47(1) |
| C(41') | 3459(7) | −3992(11) | 238(3) | 57(2) |
| C(5') | 4285(6) | −324(9) | 780(3) | 36(2) |
| C(6') | 4648(6) | 1401(9) | 1085(3) | 38(2) |

TABLE VI

Data Pertinent to the Molecular Geometry and Packing of Combretastatin A-1

| Bond Lengths. Å | |
|---|---|
| Ring C—C in range | 1.366(9)–1.401(9) |
| C(ring) —O in range | 1.375(8)–1.389(8) |
| O—C(methyl) in range | 1.413(8)–1.434(8) |

TABLE VI-continued

Data Pertinent to the Molecular Geometry and Packing of Combretastatin A-1

| Olefin | |
|---|---|
| C(1a)–C(1'a) | 1.326(9) |
| C(1)–C(1a) | 1.471(9) |
| C(1')–C(1'a) | 1.482(9) |
| Bond Angles. ° | |
| Ring C—C—C in range | 116.1(6)–122.7(6) |
| C(ring)-O—C(methyl) in range | 114.4(5)–118.6(5) |
| C(ring)-C-(ring)-O in range | 114.5(5)–124.9(5) |
| C(1)–C(1a)–C(1'a) | 131.4(6) |
| C(1a–C(1a'a)–C(1') | 130.4(6) |
| Torsion angles. ° | |
| C((6)–C(1')–C(1'a)–C(1a) | −16910 |
| C(1')–C(1'a)–C(1a)–C(1) | −6(1) |
| C(1'a)–C(1a)–C(1)–C(6) | −58(1) |
| Equations of Planes | |
| C(1)–C(2)–C(3)–C(4)–C(5)–C(6) | −.272x − .528y − .805z = −6.51 |
| C(1')–C(2')–C(3')–C(4')–C(5')–C(6') | −.489x + .533y − .691z = 3.444 |

Non-bonded contacts, Å (symmetry coordinate applied to second atom)

| | | |
|---|---|---|
| O(2') ... O(4) | 3.242(6) | x − 1, y, z |
| O(2') ... O(5) | 2.924(6) | x + 1, y, z |
| O(3') ... O(3) | 3.211(6) | x − 1, y − 1, z |

EXAMPLE 8

Synthesis of 2,3,-dihydroxy-4-methoxy-benzaldehyde

To a vigorously stirred solution of sodium boratedecahydrate (borax, 30 g) in 600 mL of water was added 2,3,4-trihydroxy-benzaldehyde (5 g, 32.4 mmol). The yellow solution was stirred at room temperature for 30 min followed by dropwise and simultaneous addition (over 30 min) of sodium hydroxide (4.0 g, 100 mmol) in water (50 mL) and dimethylsulfate (9.45 mL, 100 mmol). Vigorous stirring was continued overnight and conc. hydrochloric acid was added to pH 1. After stirring for an additional 30 min the mixture was extracted with chloroform (5×300 ml). The organic layer was once washed with brine, dried and evaporated to yield a slightly yellowish solid which on crystallization from ethyl acetate-hexane afforded slightly yellowish colored needles (3.9 g, 72%), mp 116°–17° C.: (lit. 118°–119° C.), IR (film) 3374, 1646, 1505, 1461, 1443, 1278, 1210, 1106, 636 cm⁻¹; ¹H-NMR 3.987 (3H, s, OCH₃), 5,466 (1H, brs, OH-3, D₂O exchanged) 6.617 (1H, d, $J_{AB}$=8.62, H-5), 7.147 (1H, d, $J_{BA}$=8.62 HZ, H-6, 9,757 (1H, S, CHO) 11,113 (1H, brs, OH-2, D₂O exchanged); and HREIMS (m/z, 168.0419 (M, 100%; calcd 168.0423 for C₈H₈O₄).

EXAMPLE 9

Acetylation of 2,3-dihydroxy-4-methoxy-benzaldehyde

The diphenol prepared pursuant to Example 8 (100 mg) was acetylated with acetic anhydride-pyridine to afford the diacetate as crystals from acetone-hexane: mp 126.5°–28.5° C. IR (film) 1772, 1693, 1609, 1506, 1459, 1370, 1295, 1202, 1174, 1101 and 807 cm⁻¹; ¹H-NMR (400 MHz) 2,331

(3H, s, COCH$_3$), 2,386 (3H, s, COCH$_3$), 3,927 (3H, s, OCH$_3$), 6,982 (1H, d, J$_{AB}$=8.8HZ, H-B), 7.749 (1H, d, J$_{BA}$=8.8 HZ, H-6), 9.907 (1H, S, CHO); and HRIEMS (m/z) 210.0524 (M, 20%, calcd C$_{10}$H$_{10}$O$_5$ for 210.0528 and 168.0417 (100% [M+H] COCH$_3$, C$_8$H$_8$O$_4$). Anal. calcd for C$_{12}$H$_{12}$O$_6$, C, 57.15; H, 4.75. Found: C, 57.18; H, 4.75.

EXAMPLE 10

3,4,5-trimethoxy-benzyltriphenylphosphonium bromide

A solution of triphenylphosphonium (4.2 g) in toluene (10 mL) was added to a stirred solution of 3,4,5-trimethoxybenzyl bromide (4.0 g) in toluene (15 mL) and stirring was continued for 24 hours. The phosphonium bromide that separated (8.0 g, 99%) was collected and dried under vacuum, mp 223–4 (lit 222°–23° C.).

EXAMPLE 11

2,3,-Bis[(tert-butyldimethylsilyl)-oxy]-4-methoxy-benzaldehyde

Diisopropylethylamine (1.6 mL, 9.0 mmol) was added to a stirred solution (under argon) of 2,3-dihydroxy-4-methoxybenzaldehyde (0.50 g, 2.98 mmol) in dimethylformamide (5 mL) followed by tert-butyldimethylsilyl chloride (1.0 g, 6.66 mmol). The reaction mixture was stirred at room temperature for 20 min. Ice (10 g) was added and the mixture was extracted with ether (3×15 mL). The ethereal solution was washed with water (15 mL), saturated sodium bicarbonate (2×10 mL), water (20 mL), and solvent evaporated to yield silyl ether as a chromatographically homogeneous oil (1.15 g, quantitative) that crystallized from methanol: mp 74.5°–76° C.; IR (film) 2931, 1684, 1586, 1454, 1292, 1264, 1099, 843, 827 cm$^{-1}$; $^1$H-NMR, 0.132 (12H, s, 4×SiCH$_3$), 0.987 (9H, s, 3×CH$_3$), 1.038 (9H, s, 3×CH$_3$), 1.038 (9H, s, 3×CH$_3$), 6.612 (1H, d, J$_{AB}$=8.7 HZ, H-5), 7.483 (1H, d, J$_{BA}$=8.7 HZ, H-6), 10.225 (1H, s, CHO); and HREIMS (m/z) 381.1915 (5, M CH$_3$, calcd 381.1917 for C$_{19}$H$_{33}$O$_4$Si$_2$), 339.1429 (100, M C$_4$H$_9$, calcd 339.1448 for C$_{16}$H$_{27}$O$_4$Si$_2$). Anal. calcd for C$_{20}$H$_{36}$O$_4$Si$_2$, C 60.56; H, 9.15. Found: C, 60.38; H, 9.28.

EXAMPLE 12

2',3'-Bis-[(tert-butyldimethylsilyl)-oxy-(Z) and (E) -Combretastatin A-1 Synthetic Procedure Butyllithium (20 mL, 1.5M in hexane, 30 mmol) was added (under argon) to a suspension of 3,4,5-trimethoxy-benzyl-triphenyl-phosphonium bromide (15.7 g, 30 mmol ) in tetrahydrofuran (450 mL) at −15°. The resulting deep reddish solution was allowed to stir at room temperature for 30 min. Aldehyde (11.09 g, 28.0 mmol) was added and the reaction mixture was diluted with ice-cold water and extracted with ether (3×250 mL). The ethereal solution was washed with water and solvent was evaporated to yield a crude product which was crystallized from ethanol to afford pure Z-isomer (11.0 g) and a mixture (1:1, by H-NMR) of Z/E isomer (3.5 g, total yield 92.5%). The Z-isomer recrystallized from methanol-ethyl acetate to furnish colorless needles: mp 117°–18° C.; IR (film) 1580, 1507, 1496, 1472, 1456, 1445, 1420, 1248, 1129, 1102, 1010, 840, 780 cm$^{-1}$ $^1$H-NMR (400 MHz) 0.105 (6H, s, 2X Si-CH$_3$), 0.190 (6H, s, 2×SiCH$_3$), 0.999 (9H, s, 3×CH$_3$), 1.038 (9H, s, 3×CH$_3$), 3.674 (6H, s, 2×OCH$_3$), 3.738 (3H, s, OCH$_3$) 3.835 (3H, s, OCH$_3$), 6.358 (1H, d, J$_{A'B'}$=12.0 Hz, CH=CH—), 6.361 (1H, d, J$_{AB}$=8.7 Hz H-5'), 6.584 (1H, d, J$_{B'A}$=12.4 Hz, —CH=CH—), 6.619 (2H, S, H-2, 6), 6.910 (1H, d, J$_{BA}$=8.7 Hz, H-6'); and HREIMS (m/z) 560.2941 (90%, m, calcd 560.2989 for C$_{30}$H$_{48}$O$_6$Si$_2$), 488.2060 (100, M C$_5$H$_{12}$, C$_{25}$H$_{36}$O$_6$Si$_2$). Anal. calcd for C$_{30}$H$_{48}$O$_6$Si$_2$, C, 64.25; H, 8.63. Found: C, 64.03; H, 8.70.

EXAMPLE 13

Purified E-isomer

A small portion of the Z/E mixture produced according to Example 12 was chromatographed on a SILICA GEL column and eluted with hexane-ethyl acetate (49:1). The fraction enriched with the E-isomer crystallized from methanol-ethyl acetate to afford pure E-isomer as colorless plates melting at 139°–40° C.: IR (film) 1581, 1507, 1496, 1472, 1463, 1456, 1444, 1239, 1130, 1101, 840, 785 cm$^{-1}$; $^1$H-NMR (400 MHz) 0.114 (6H, s, 2×SiCH$_3$), 0.133 (6H, s, 2×SiCH$_3$), 0.999 (9H, s, 3×CH$_3$), 1.092 (9H, s, 3×CH$_3$), 3.793 (3H, s, OCH$_3$), 3.862 (3H, s, OCH$_3$), 3.884 (6H, s, 2×OCH$_3$), 6.556 (1H, d, J$_{AB}$=8.72 HZ, H-5'), 6.716 (2h, S, 6) 6.805 (1H, d, J$_{A'B'}$=16.44 Hz, —CH=CH—), 7.198 (1H, d, J$_{BA}$=8.72 Hz, H-6'), 7.308 (1H, d, J$_{B'A}$=16.44 Hz, —CH=CH—); and HREIMS (m/z) 560.3151 (100, M Calcd C$_{30}$H$_{48}$O$_6$Si$_2$), Anal. calcd for C$_{30}$H$_{48}$O$_6$Si$_2$ ½ H$_2$O: C, 63.23; H, 8.66. Found: C, 63.32.

EXAMPLE 14

Z and E Isomers

In another experiment, when 1.5 equivalents of n-butyl-lithium was used per equivalent of phosphonium bromide, the ratio of Z/E isomer changed dramatically from 9:1 to 3:5:1.

EXAMPLE 15

$^{31}$P-NMR Evaluation

Phosphonium bromide (0.523 g, 1.0 mmol) in dry tetrahydrofuran (20 mL was treated (under argon) with 1.0 molar equivalent of n-butyllithium at −15° to generate the ylide. An aliquot (2.0 mL, 0.10 mmol) of the ylide solution was transferred to an NMR tube (10 mm) and frozen (liquid nitrogen). A solution of aldehyde (5d, 39.0 mg, 0.098 mmol) in tetrahydrofuran-d$_8$ (1 mL) was added and the frozen sample was warmed to −80° in the NMR probe. Examination of the spectrum (at −80° showed three sharp singlets at δ 24.538 (ylide), 7.553 (cis oxaphophetane) and δ 8.0 ppm (trans oxaphosphetane) integrating in the ratio 15:65:1 respectively. On warming to 60° during 10 min the cis-oxaphosphetane was formed at the expense of the ylide and the ratio changed to 9:65:1. While disappearance of the ylide was still in progress, a new broad singlet started appearing (−50°, 10 min) at 28.4 ppmm, dye to formation of triphenylphosphine oxide (as a lithium bromide complex) the trans oxaphosphetane signal disappeared and the ratio of signals from downfield to upfield was 11:3:64:0. The disappearance of cis oxaphosphetane and appearance of triphenylphosphine oxide was monitored at −30° (10 minutes after −50°) and −10° (12 minutes after −30°) to give the ratios 11:23 and 33:18 respectively. After another 12 minutes at 25° C. the oxaphosphetane disappeared completely. The results clearly indicate that there was no interconversions of cis to trans oxaphosphatanes. The 10% of E-isomer may have been formed due to isomerization during isolation. The shift of $^{31}P$ in the triphenylphosphine oxide lithium bromide complex was found to change with temperature as follows: –50° (28.4), –30° (28.0 used as reference per Reitz et al., *J. Am. Chem. Soc.*, 1984, 106, 1873), –10° (27.9), and 25° (26.3).

EXAMPLE 16

2'3'-diacetoxy-4'-methoxy-Z-combretastatin A-1

To a 1.8 g sample of the isomer mixture in tetrahydrofuran (10 mL) was added tetrabutylammonium fluoride 8 mL of a 1M solution in tetrahydrofuran and the mixture was stirred (under argon) at room temperature for 15 minutes. Ethyl ether (50 mL) was added and the solution was washed with water (2×50 mL) and the solvent removed under reduced pressure. The residue was acetylated in 4 mL of 1:1 acetic anhydride-pyridine. After stirring overnight the acetylation mixture was poured into ice-water, extracted with ether (3×50 mL), washed successively with 1N-hydrochloric acid (2×25 mL) saturated sodium bicarbonate solution (2×25 mL) and water (50 mL). Removal solvent furnished a gummy residue which was chromatographed on a column of SILICA GEL (50 g). Gradient elution with hexane-ethyl acetate (9:1→1:1) afforded 0.55 g of Z-isomer, and 0.60 g of E-isomer. The Z-isomer was recrystallized from hexane-ethyl acetate to give colorless prisms, mp 133°–35° identical and diacetate prepared from natural combretastatin A-1. Anal. calcd for $C_{22}H_{24}O_8$: C, 63.46; H, 5.81. Found: C, 63.37; H, 5.79.

EXAMPLE 17

2'3'-diacetoxy-4'methoxy-E-combretastatin A-1

The E-isomer collected from Example 16 was recrystallized as needles mp 172°–73° C. from hexane-ethyl acetate: IR (film) 1775, 1582, 1507, 1455, 1295, 1206, 1173, 1126, 1089, 670 cm$^{-1}$ $^1$H-NMR (400 MHz) 2.313 (3H, s, COCH$_3$), 2.348 (3H, s, COCH$_3$), 3.863 (6H, s, 2×OCH$_3$), 3.897 (3H, s, OCH$_3$), 3.899 (3H, s, OCH$_3$), 6.669 (2H, s, H-2, 6), 6.870 (1H, d, $J_{AB}$=16.02 Hz, —CH=CH—), 6.897 (1H, d, $J_{A'B'}$= 8.5 HZ, H-5'), 6.917 (1H, d, $J_{BA}$=16.02 HZ, —CH=CH—), 7.470 (1H, d, $J_{B'A}$=8.5 HZ, H-6') and HREIMS (m/z) 416.1486 (33, M, calcd 416.1471 for $C_{22}H_{24}O_8$), 374, 1347, (39, M+H OOCH$_3$), 332.1234 (46, M+2H–2×CH$_3$CO) Anal calcd for $C_{22}H_{24}O_8$ ½ $H_2O$, C, 62.11; H, 5.92. Found: C, 62.27; H, 5.73.

EXAMPLE 18

Combretastatin A-1

Method A. A 60 mg sample of the synthetic diacetate in methanol (3 mL) was stirred (under argon) with potassium carbonate (50 mg) for 1 hour. Hydrochloric acid (1N was added and the phenol was extracted with chloroform (3×10 mL), washed with water (10 mL) and solvent removed. The product was passed through a pipette of silica gel (1.0 g) to yield combretastatin A-1 (45 mg 94%). The viscous oil crystallized from hexanechloroform to afford a pure specimen as plates, mp 114°–15° identical with the natural product.

EXAMPLE 19

Combretastatin A-1

Method B. A solution of silyl ether (10.78 g 19.26 mmol) in tetrahydrofuran (100 mL under argon) was treated with tetrabutylammonium fluoride (45 mL, 1M solution in tetrahydrofuran) and stirred for 10 minutes. After completion the reaction mixture was extracted with ether (300 mL). The ethereal solution was washed with cold water (2×100 mL), dried and evaporated to a powder (1a, 6.0 g, 93.8%), which crystallized from chloroform-hexane as plates, mp 113°–15°. Anal. calcd for $C_{18}H_{20}O_6$, C, 65.06; H 6.07. Found: C, 64.48; H, 6.03.

EXAMPLE 20

Microtubule Assembly

The assembly reaction at 37° C. was followed turbidimetrically as described by Hamel et al, *Biochem. Pharmacal.*, 32, p. 3864, 1983; and Batra et al, *Molecular Pharm.* 27, pP 94–102, 1984. Each 0.25 ml reaction mixture contained 1.5 mg/ml of tubulin and 0.5 mg/ml of microtubule-associated proteins (proteins were purified as described by Hamel et al, *Biochemistry*, 23, p. 4173, 1984, 0.1M 4-morpholine ethanesulfonate (adjusted to pH 6.6 with NaOH), 0.5 mM $MgCl_2$, 0.5 mM guanosine 5'-triphosphate, and drugs as required. The concentration of drug needed to inhibit the extent of assembly by 50% was determined.

EXAMPLE 21

Binding of [$^3$H]colchicine to tubulin

Binding of radiolabeled colchicine to tubulin was measured by retention of drug-tubulin complex on DEAE-cellulose paper filters, as described by Hamel et al, *Biochem. Pharmacal.*, supra, Reaction mixtures (0.1 ml) contained 0.1 mg/ml of tubulin, 5 µM [$^3$H]colchicine, the competing drug at 5 µM, 1.0M monosodium glutamate (adjusted to pH 6.6 with HCl), 0.1M glucose-1-phosphate, 1 mM $MgCl_2$, 1 mM guanosine 5'-triphosphate, and 0.5 mg/ml bovine serum albumin (the latter four components substantially enhance the rate of the reaction). Incubation was for 10 minutes at 37° C.

EXAMPLE 22

Acetylation of Combretastatin A-2 and A-3

Both combretastatin A-2 (12.0 mg) and combretastatin A-3 (18.0 mg) were acetylated (separately) with acetic anhydride (1.0 ml)—pyridine (0.5 ml) at room temperature (72 hrs). Solvent was evaporated under a stream of nitrogen to afford the acetate and diacetate as viscous oils: Combretastatin A-2 acetate displayed Rf. 0.60 (1:1 hexane-ethyl acetate); IR $\lambda_{max}$ (NaCl) 1767, 1510, 1430, 1264, 1199, 1127, 1112, 1086, 1042, 930, 773 cm$^{-1}$; $^1$H-NMR (400 MHz) 2.273 (3H, s, COCH$_3$), 3,731 (3H, s, OCH$_3$), 3.809 (3H, s, OCH$_3$), 5.940 (2H, s, —OCH$_2$O—), 6.410 (2H, s, CH=CH—), 6.453 (1H, d, J=1.1 Hz, H-2, or H-6), 6.473 (1H, d, J=1.1 Hz, H-6 or H-2), 6,840 (1H, d, J=8.56 Hz, H-5'), 6.977 (1H, d, J=2.0 Hz, H-2'), 7.107 (1H, d, J=8.56, 2.0 Hz, H-6'), HREIMS (m/z) 342.1101 (59, M$^+$, calcd for $C_{19}H_{18}O_6$: 342.1103, 300.0987 (100, $C_{17}H_{16}O_5$); and Combretastatin A-3 diacetate displayed Rf. 0.54 (1:1 hexane-ethyl acetate); IR $\lambda_{max}$ (NaCl) 1769, 1510, 1370, 1284, 1265, 1242, 1203, 1132, 1113, 1092 cm$^{-1}$; $^1$H-NMR (400

MHz) 2.270 (3H, s, COCH$_3$), 3,813 (3H, s, OCH$_3$), 6.390 (1H, d, J=12.1 Hz, —CH=CH—), 6.445 (1H, d, J=12.2 Hz, —CH=CH—), 6,634 (1H, d, J=8.46 Hz, H-5'), 7.037 (1H, d, J=2.0 Hz, H-2'), 7.115 (1H, dd, J=8.46, 2.0 Hz, H-6'); HREIMS (m/z) 386.1365 (71, M$^+$, calcd for C$_{21}$H$_{22}$O$_7$: 386.1366), 344.1252 (56, C$_{19}$H$_{20}$O$_6$), 302.1146 (100, C$_{17}$H$_{18}$O$_5$).

EXAMPLE 23

Hydrogenation of Combretastatin A-2 and Combretastatin A-3

In separate experiments combretastatin A-2 (12.0 mg) and combretastatin A-3 (10 mg) in methanol (10 ml) and 5% Pd/c (10 mg) were each treated with a positive pressure of hydrogen at ambient temperature overnight. Catalyst was removed by filtering the solution and the product purified by preparative layer chromatography on regular (250μ) ANAL-TEX plates with hexane-ethyl acetate (1:1) as mobile phase. The oily product from combretastatin A-3 was identical with natural combretastatin B-2 while the dihydro product i.e., bibenzyl, from combretastatin A-2 was a viscous oil exhibiting Rf. 0.58 (1:1, hexane-ethyl acetate); IR $\lambda_{max}$ (NaCl) 3478, 1633, 1590, 1510, 1451, 1441, 1329, 1274, 1194, 1129, 1089, 925 cm$^{-1}$; $^1$H-NMR (90 MHz) 2.78 (4H, s, —CH$_2$CH$_2$—), 3.86 (3H, s, OCH$_3$), 3.87 (3H, s, OCH$_3$), 5.93 (2H, s, —OCH$_2$O—), 6.30 (H, d, J=1.5 Hz, H-2 or H-6), 6.38 (1H, d, J=1.5 Hz, H-6 or H-2), 6.63 (1H, dd, J=8.2, 1.9 Hz, H-6'), 6.76 (1H, d, J=8.2 Hz, H-5'), 6.77 (1H, d, J=1.9 Hz, H-2'); an HREIMS (m/z) 302.1149 (29, M$^+$, calcd for C$_{17}$H$_{18}$O$_5$: 302.1154), 165.0547 (100, calcd for C$_9$H$_9$O$_3$: 165.0552), 137.0597 (67, calcd for C$_8$H$_9$O$_2$: 137.0603).

EXAMPLE 24

Combretastatin A-2/3'-O-p-bromophenylcarbamate

To a solution of combretastatin A-2 (10 mg) in dry methylene chloride (1 ml) was added to a solution of p-bromophenyl isocyanate (80 mg) in methylene chloride (1 ml). The mixture was stirred for 5 days at room temperature and heated at reflux for 24 hours. The reaction mixture was cooled to room temperature and the solution filtered. The filtrate was concentrated and chromatographed by preparative layer with hexane-ethyl acetate (1:1) as mobile phase. The band was eluted with acetone and crystallized from methylene chloride to afford an amorphous powder, mp 138°–140°: IR $\lambda_{max}$ (NaCl) 3310, 1734, 1722, 1533, 1509, 1491, 1431, 1398, 1202, 1128, 1114, 924, 750 cm$^-$; $^1$H-NMR (90 MHz), 3.75 (3H, s, (OCH$_3$), 3.94 (3H, s, OCH$_3$), 5.93 (2H, s, OCH$_2$O), 6.43 (2H, brs, —CH=CH—), 6.48 (2H, AB$_q$, J=1.1 Hz, H-2, H-6), 6.65–7.0 (3H, M, H-2', 5', 6'), 7.09 (1H, s, NH), 7.35 (2H, d, J=8.5 Hz, ArH), 7.41 (2H, d, J=8.5 Hz, ArH). HRFAB: 500, 498.055218 (M++H, calcd for C$_{24}$H$_{21}$O$_6$ NBr$^{79}$: 498.058850).

EXAMPLE 25

Methyl-3,4-dihydroxy-5-methoxy-benzoate

Methyl gallate (10 g, 54.3 mmol) was added to a solution of borax (80 g) in 800 ml of water with stirring (30 min.). Dimethyl sulfate (30 ml) and solution of sodium hydroxide (13 g in 50 ml of water) were added from two separate dropping funnels over 2.5 hours and stirring was continued overnight. Concentrated sulfuric acid (50 ml) was added and stirring continued for an additional hour. The product was extracted with chloroform (5×11 and each time stirring the solution for 20 minutes). The combined chloroform extract was washed with brine (500 ml), dried, concentrated and the residue crystallized from methanol-benzene to yield methyl ether (9.1 g, 84.5%): mp 110°–111° (lit.$^{19}$ mp 112°); IR $\lambda_{max}$ (NaCl) 3380, 1700, 1696, 1611, 1436, 1341, 1314, 1229, 1204, 1089 cm$^{-1}$; and $^1$H-NMR (90 MHz), 3.88 (3H, s, OCH$_3$), 3.94 (3H, s, OCH$_3$), 5.50–6.0 (2H, OH), 7.22 (1H, d, J=1.8 Hz, ArH), 7.34 (1H, d, J=1.8 Hz, ArH). Under analogous experimental conditions but using continuous extraction with ethyl acetate in place of chloroform, mixture of methyl gallate (7.0 g) and 3-O-methyl-gallic acid (1.4 g) was obtained.

EXAMPLE 26

Methyl 3,4-methylenedioxy-5-methoxy-benzoate

Cesium fluoride (24.5 g, 161.5 mmol) was added to a stirring solution of the phenol prepared in Example 25 (7.3 g, 36.8 mmol) in dimethylformamide (90 ml) under argon. After stirring 20 minutes, dibromomethane (2.8 ml, 40.5 mmol) was added and the mixture heated for 2 hours. The reaction was allowed to cool to room temperature. Ether (300 ml) was added and the ethereal solution was washed with cold water (3×50 ml), dried and concentrated to afford the methylenedioxy derivative as a powder (7.62 g, 98% yield), which was recrystallized from acetonehexane, mp 89°–91°: IR $\lambda_{max}$ (NaCl) 1714, 1636, 1507, 1436, 1369, 1327, 1245, 1177, 1107, 1041 cm$^{-1}$; $^1$H-NMR (90 MHz) 3.89 (3H, s, OCH$_3$), 6.06 (2H, s, —CH$_2$—), 7.21 (1H, d, J=1.4 Hz, ArH), 7.33 (1H, d, J=1.4 Hz, ArH) and EIMS, m/z (rel. int/%) 210 (100, M+), 179, M+-OCH$_3$). Anal. Calcd for C$_{10}$H$_{10}$O$_5$: C, 57.15; H, 4.80 Found: C, 57.10; H, 4.74.

EXAMPLE 27

3,4-Methylenedioxy-5-methoxy-benzyl alcohol

Lithium aluminum hydride (0.50 g) was added to a stirred solution of the methyl ester prepared in Example 26 (1.7 g) in ether-tetrahydrofuran (2:1, 50 ml). After stirring for 30 minutes, the reaction mixture was cooled to 5° C. and saturated aqueous sodium sulfate was carefully added until a white solid appeared. The precipitate was collected by filtration and the solution was dried and solvent evaporated to give crystalline benzyl alcohol (1.45 g, 98% yield). Recrystallization from ethyl acetate-hexane afforded an analytical sample melting at 66°–67° C. (lit.$^{21}$ mp 66): IR $\nu_{max}$ (NaCl) 3220, 1632, 1467, 1453, 1323, 1203, 1133, 1093, 1008, 918 cm$^{-1}$; and $^1$H-NMR (90 MHz) 1.75 (1H, brs, OH), 3.90 (3H, s, OCH$_3$), 4.58 (2H, brs, —CH$_2$OH), 5.96 (2H, s, —CH$_2$—), 6.55 (2H, s, ArH).

EXAMPLE 28

3,4-Methylenedioxy-5-methoxy-benzaldehyde

To a stirred yellow mixture of pyridinium chlorochromate (1.72 g, 7.99 mmol) and anhydrous sodium acetate (0.655 g, 7.99 mmol) in CH$_2$Cl$_2$ (30 ml) was added at once a solution of benzyl alcohol 7e (1.32 g, 7.26 mmol) in CH$_2$Cl$_2$ (10 mol). The greyish solution which formed immediately was stirred for 2 hours, and the reaction was monitored by TLC (1:1 hexane-ethyl acetate). After filtering the solution through a small SILICA GEL column colorless aldehyde (1.18 g, 91% yield) was eluted with hexane-ethyl acetate (7:3). Recrystallization from acetone afforded needles, mp 132°–133° C. (lit. mp 130–31, 129–30): IR $v_{max}$ (NaCl) 1694, 1676, 1622, 1508, 1474, 1451, 1362, 1325, 1134, 1190 cm$^{-1}$; and $^1$H-NMR (90 MHz), 3.95 (3H, s, OCH$_3$), 6.09 (2H, s, —CH$_2$—), 7.04 (1H, d, J-1.4 Hz, ArH), 7.12 (1H, d, J=1.4 Hz, ArH), 9.78 (1H, s, —CHO).

EXAMPLE 29

3-Hydroxy-4-methoxy-benzyl-triphenylphosphonium/bromide

A solution of phosphorus tribromide (8.51 ml) in a mixture of tetrahydrofuran-benzene (1:2, 330 ml) was added to a cool (0° C.) solution of 3-hydroxy-4-methoxy-benzyl alcohol (6.13 g, 40 mmol) in the same solvent (75 ml) under argon. The colorless solution was stirred at room temperature for 2 hours, poured onto ice water (100 ml) and extracted with ether (2×100 ml). The ethereal layer was washed once with water (50 ml), followed by brine (2×50 ml), dried and evaporated to dryness to afford the bromide as an amorphous powder. A solution prepared from the crude bromide, anhydrous-benzene (150 ml) and triphenylphosphine (15.72 g, 60 mmol) was stirred for 10 minutes at room temperature and heated at reflux for 2 hours. On cooling to room temperature, a viscous oil separated. The upper solvent phase was decanted and the oil was crystallized from ethanol-ether to give the bromide as a powder (10.0 g, 52.4% from alcohol): mp 262°–4° C.; IR $v_{max}$ (NaCl) 3158, 1604, 1589, 1527, 1512, 1437, 1279, 1255, 1128, 1111, 743 cm$^{-1}$; and $^1$H-NMR (90 MHz, CDCl$_3$+D$_2$O), 3.77 (3H, s, OCH$_3$), 4.95 (2H, d, $J_{PCCH}$=13.7 Hz, —CH$_2$—), 6.57 (2H, brs, ArH)), 6.83 (1H, brs, ArH), 7.56–7.77 (15H, ArH). Anal. Calcd for C$_{26}$H$_{24}$O$_2$PB$_r$: C, 65.6; H, 5.05; Br, 16.67. Found C, 64.50; H, 5.07; Br, 16.78.

EXAMPLE 30

1-Hydroxy-3,4-methylenedioxy-4',5-dimethoxy-(E)-and (Z)-stilbene, Combretastatin A-2 and E-isomer Phosphonium bromide (3.35 g, 7.0 mmol) was suspended in tetrahydrofuran (100 ml), stirred, cooled to –50° C. (under argon), and n-butyllithium (10 ml, 15 mmol) was added using a syringe and septum technique. The solution became deep red immediately and upon reaching room temperature was stirred 20 minutes prior to adding a solution of the aldehyde obtained from Example 28 (1.15 g, 6.39 mmol) in tetrahydrofuran (30 ml). All the aldehyde was consumed in 30 minutes. Cold hydrochloric acid (1N, 50 ml) was added followed by water (100 ml), and the product was extracted with ethyl acetate (3×100 ml) from the colorless solution. The ethyl acetate extract was washed with water (50 ml), brine (50 ml), dried and solvent evaporated. The crude product was chromatographed on a SILICA GEL (50 g) column. Elution with hexane-ethyl acetate (17:3) afforded a mixture of Z and E stilbenes (1.09 g, 57% yield, ratio Z/E, 1:16). Half of the product was rechromatographed on a longer SILICA GEL column and elution with hexane-ethyl acetate (9:1) provided first combretastatin A-2 (40 mg) as a viscous oil identical with natural combretastatin A-2 and later the E-isomer (0.20 g) as needles from ethyl acetate-hexane, mp 145°–50° C.: IR $v_{max}$ (NaCl) 3490, 1622, 11509, 1463, 1440, 1429, 1319, 1279, 1263, 1254, 1133 cm$^{-1}$; and $^1$H-NMR (400 MHz) 3.908 (3H, s, OCH$_3$), 3.941 (3H, s, OCH$_3$), 5.598 (1H, brs, OH), 5.978 (2H, s, —OCH$_2$O—), 6.629 (1H, d, J=1.30 Hz, H-2 or H-6), 6.729 (1H, d, J=1.30 Hz, H-6 or H-2), 6.825 (1H, d, J=8.32 Hz, H-5'), 6.848 (2H, s, —CH=CH—), 6.945 (1H, d, J=8.32, 2.0 Hz, H-6'), 7.113 (1H, d, J=2.0 Hz, H-2').

Anal. Calcd for C$_{17}$H$_{16}$O$_5$: C, 68.00; H, 5.37. Found C, 67.63; H, 5.37.

EXAMPLE 31

Photochemical isomerization of E-stilbene to combretastatin A-2

A solution of E-isomer (40 mg) in dioxane (30 ml) and water (1 ml) was stirred and irradiated (directly into the solution from above) with long wave (365 nm) length UV for 5 hours. The ultraviolet source was UV lamp used for visualizing TLC plates equipped with both short-wave (254 nm) and long wave (365 nm) lamps. The solvent was removed and $^1$H-NMR examination of the residue revealed an isometric mixture in the ratio Z/E of 2.5:1.5. Separation by chromatography on a SILICA GEL column and elution with hexane-ethyl acetate (9:1) yielded combretastatin A-2 (15 mg).

EXAMPLE 32

(tert-Butyldimethylsilyl) 3-[(tert-Butyldimethylsilyl)-oxy]-4,5,-dimethoxy-benzoate Diisopropylethylamine (11.3 ml, 77 mmol) was added to a stirred solution of 3-hydroxy-4,5-dimethoxy-benzoic acid (5.0 g, 25 mmol) in dimethylformamide (50 ml, under argon) followed by addition of tert-butyldimethylsilyl chloride (8.32 g, 55 mmol) and the reaction mixture was stirred for 1 hour. Ice (50 g) was added and the reaction mixture was extracted with ethyl ether (200 ml). The ethereal solution was washed with cold water (3×50 ml), sodium bicarbonate solution (10%, 50 ml), water (3×50 ml), dried and solvent evaporated to yield tert-butyldimethylsilyl 3-[(tert-Butyldimethylsilyl)-oxy]-4,5,-dimethoxy-benzoate as a chromatographically homogeneous oil (10.4 g, 97% yield). Attempts at high vacuum distillation (100° at 1.0 mm/Hg) failed and resulted in desilylation. However, the oil showed the correct IR and $^1$H-NMR spectral data for the silane: IR $v_{max}$ (NaCl) 2932, 1700, 1590, 1420, 1350, 1254, 1230, 1221, 1118, 839, 775 cm$^{-1}$ and $^1$H-NMR (90 MHz) 0.107 (6H, s, 2×SiCH$_3$), 0.276 (6H, s, 2 × SiCH$_3$), 0.922 (18H, s, 6 ×CH$_3$), 3.751 (3H, s, OCH$_3$), 3.790 (3H, s, OCH$_3$), 7.170 (2H, AB$_q$, J$_{AB}$=1.5 Hz, ArH).

EXAMPLE 33

3-[(tert-Butyldimethylsilyl)-oxy]-4,4,-dimethoxy-benzyl alcohol

The silyl ester (10.0 g, 23 mmol) was dissolved in ether (300 ml) and stirred (under argon) with lithium aluminum hydride (2.0 g) at room temperature for 1 hour. Saturated ammonium chloride solution (ice-cold) was added and the ether layer separated. The aqueous phase was extracted with ether (3×200 ml) and the combined ether extract was washed with sodium bicarbonate solution, cold water, and dried. After solvent removal, the residual oil was found to be chromatographically homogeneous alcohol (6.0 g, 86% yield): the oil distilled at 210° C. (0.04 mm) and displayed IR $v_{max}$ (NaCl) 3450, 2931, 1587, 1501, 1427, 1233, 1118, 1004, 837, 782 cm$^{-1}$; and $^1$H-NMR (90 MHz) 0.201 (6H, s, 2 × CH$_3$), 1.026 (9H, s, 3×CH$_3$), 1.716 (1H, t, J=5.9 Hz, OH D$_2$O exchanged) 3.794 (3H, s, OCH$_3$), 4.596 (2H, d, J=5.9

Hz, —CH$_2$OH, collapsed to a broad singlet upon D$_2$O exchange), 6.510 (1H, d, J=1.9 Hz, ArH), 6.610 (1H, d, J=1.9 Hz, ArH). Anal. Calcd for C$_{16}$H$_{26}$O$_4$Si: C, 60.39, H, 8.78 Found C, 60.06; H, 8.78.

EXAMPLE 34

3-[(tert-Butyldimethylsilyl)-oxy]-4,5,-dimethoxy-benzyl-bromide

Before adding phosphorus tribomide (0.95 ml) in methylene chloride (5 ml) a solution of the silyoxy-benzyl alcohol prepared in Example 33 (6.0, 20 mmol) in methylene chloride (anhydrous, 100 ml) was stirred and cooled (−10°, ice-salt bath) for 15 minutes. The mixture was stirred 10 minutes and 10% aqueous sodium bicarbonate solution (50 ml) was added (slowly). The methylene chloride layer was watched with cold water (2×50 ml), dried and solvent evaporated to give 3-[(tert-Butyldimethylsilyl)-oxy]-4,5,-dimethoxy-benzyl-bromide as a colorless oil (6.4 g, 88% yielded), homogeneous by TLC. While the product thus formed was heat sensitive, and distillation was unsuccessful, it did give the correct IR $\nu_{max}$ (NaCl) 2932, 1586, 1500, 1427, 1348, 1250, 1234, 1227, 1111, 838 cm$^{-1}$; $^1$H-NMR (90 MHz), 0.183 (6H, s, 2×CH$_3$), 1.006 (9H, s, 3×CH$_3$), 3.777 (3H, s, OCH$_3$), 3.855 (3H, s, OCH$_3$), 4.409 (2H, s, —CH$_2$—), 6.561 (2H, AB$_q$, J=2.0 Hz, ArH); and MS (m/z, rel. amt.) 362, 360 (50%, M$^+$) 305, 303, (80, M$^+$—C$_4$H$_9$), 281 (60, M$^+$—Br), 253 (75, M$^+$—Br—28), 209 (100, M$^+$—Br—C$_5$H$_{12}$), 166 (45, M$^+$—Br—Si(CH$_3$)$_2$C (CH$_3$)3].

EXAMPLE 35

3-[(tert-Butyldimethylsilyl)-oxy]-4,5-dimethoxy-benzyl-tri-phenylphosphonium-bromide To a solution of the bromide prepared in Example 34 (6.0 g, 16.6 mmol) in toluene (50 ml) was added (stirring) a solution of triphenylphosphine (4.36 g, 16.6 mmol) in toluene (10 ml). The mixture was heated to reflux for 15 minutes. When the clear solution started to become turbid, heating was discontinued and the mixture was stirred overnight at room temperature. The solid phosphonium bromide (7.17 g, 69% yield) was recovered by filtration as a powder at 248°; IR $\nu_{max}$ (NaCl) 2957, 1586, 1502, 1453, 1436, 1344, 1253, 1113, 836, 742, 721 cm$^{-1}$ and $^1$H-NMR (90 MHz) 0.58 (6H, s, 2×CH$_3$), 1.48 (9H, s, 3×CH$_3$), 4.15 (3H, s, OCH$_3$), 4.32 (3H, s, OCH$_3$), 5.89 (2H, d, J$_{PCH}$=14 Hz, CH$_2$), 6.71 (1H, t, J=2.2 Hz, ArH), 7.36 (1H, t, J=2.2 Hz, ArH), 8.23–8.45 (15H, ArH). Anal. Calcd for C$_{33}$H$_{40}$BrO$_3$PSi: C, 63.56; H, 6.46; Br, 12.81. Found: C, 64.04; H, 6.57; Br, 12.47.

EXAMPLE 36

Silyl-Combretastatin A-3

Butyllithium (2.47 ml, 2.2 mmol) was added to a stirred and cooled (−10° C.) suspension of phosphonium bromide (1.31 g, 2.1 mmol) in tetrahydrofuran (100 ml). The orange-red solution was stirred at room temperature 10 minutes. 3-[(tert-butyl-dimethylsilyl)-oxy]-4, methoxy-benzaldehyde (0.532 g, 2.0 mmol) was added and stirring continued another 10 minutes while the red solution changed to yellow. A TLC examination (4:1, hexane-ethyl acetate) showed completion of reaction. Ice water (100 ml) was added and the product extracted with ether (3×100 ml). The ethereal solution was washed with water (100 ml), and concentrated to a gum which upon SILICA GEL column (40 g) chromatography and elution with hexane-ethyl acetate (97:3) afforded a mixture of 3,3'-bis-[(tert-butyldimethylsilyl)-oxy], 4',4,5-trimethoxy-(Z)- and (E)-stilbene in a ratio of 5:1 (0.870 g, 82% yield). The isomers were separated by preparative layer chromatography on SILICA GEL (20×20 cm, 500 m, E-Merck plates) employing 19:1 hexane-ethyl acetate. The short UV positive upper band was major product elution with hexane-ethyl acetate yielded Z-isomer as an oil (423 mg): IR $\nu_{max}$ (NaCl) 2930, 1575, 1509, 1250, 1231, 1118, 838, 782 cm$^{-1}$ and $^1$H-NMR (400 MHz) 0.070 (6H, s, 2×CH$_3$), 0.105 (6H, s, 2×CH$_3$), 0.932 (9H, s, 3×CH$_3$), 0.958 (9H, s, 3×CH$_3$), 3.666 (3H, s, OCH$_3$), 3.761 (3H, s, OCH$_3$), 3.774 (3H, s, OCH$_3$), 6.366 (1H, d, J=12 Hz, —CH═CH—), 6.413 (1H, d, J=1.84 Hz, H-6), 6.429 (1H, d, J=12 Hz, —CH═CH—), 6.471 (1H, d, J=1.84 Hz, H-2), 6.718 (1H, d, J=8.3 Hz, H-5'), 6.778 (1H, d, J=2.0 Hz, H-2'), 6.840 (1H, dd, J=8.3, 2.0 Hz, H-6'). The lower long UV positive band was also eluted with hexane-ethyl acetate to give an E-isomer as an oil (80 mg): IR $\nu_{max}$ (NaCl) 2930, 1578, 1509, 1427, 1272, 1251, 1117, 838, 782 cm$^{-1}$ and $^1$H-NMR (400 MHz) 0.183 (6H, s, 2×CH$_3$), 0.207 (6H, s, 2×CH$_3$), 1.024 (9H, s, 3×CH$_3$), 1.028 (9H, s, 3×CH$_3$), 3.794 (3H, s, OCH$_3$), 3.823 (3H, s, OCH$_3$), 3.901 (3H, s, OCH$_3$), 6.626 (1H, d, J=1.88 Hz, H-6), 6.693 (1H, d, J=1.88 Hz, H-2), 6.800 (1H, d, J=16.2 Hz, —CH═CH—), 6.825 (1H, d, J=8.3 HZ, H-5'), 6.845 (1H, d, J=16.2 Hz, —CH═CH—), 7.020 (1H, d, J=2.100, H-2'), 7.047 (1H, dd, J=8.3 Hz, 2.1 Hz, H-6'). Anal. Calcd for C$_{29}$H$_{46}$O$_5$Si$_2$: C, 65.62; H, 8.73. Found C, 86.09; H, 8.97.

EXAMPLE 37

Combretastatin A-3

To a stirred solution of silyl-Z-stilbene (0.25 g, 0.47 mmol) in tetrahydrofuran (10 ml under argon) was added a 1M tetrahydrofuran solution of tetrabutylammonium fluoride (1 ml, 1.0 mmol). Instantaneously the solution became yellow and reaction was complete as evidenced by TLC (hexane-ethyl acetate 3:2). Ice (5 g) and water (5 ml) was added to the mixture and the product extracted with ether (2×25 ml). The ethanol extract was washed with cold water (20 ml), and dried. After evaporation of solvent the residue in 1:1 hexane-ethyl acetate was filtered through a pipette filled with SILICA GEL (2 g) to afford combretastatin A-3 as an oil (0.13 g, 91% yield), homogeneous by TLC and identical with the natural product.

EXAMPLE 38

Methylation of Combretastatins B-2 and B-3

Combretastatin B-2 (10 mg) and combretastatin B-3 (2.0 mg) were separately methylated in a refluxing (5 hr) mixture composed of excess methyl iodide, potassium carbonate and acetone. The potassium carbonate was collected by filtration and the permethyl ether derivative was isolated by passing the filtrate through a pipette filled with silica gel. The products from both reactions were found to be identical viscous oils: IR $\nu_{max}$ 1589, 1514, 1509, 1464, 1457, 1419, 1261, 1236, 1127 cm$^{-1}$; $^1$H-NMR (400 MHz) 2.849 (4H, m, ARCH$_2$), 3.825 (H, s, OCH$_3$), 3.844 (3H, s, OCH$_3$), 3.863 (3H, s, OCH$_3$), 6.368 (2H, s, ArH), 6.662 (1H, d, J=1.88 Hz, ArH), 6.724 (1H, dd, J=8.10, 1.88 Hz, ArH), 6.802 (1H, d, J=8.10 Hz, ArH); HREIMS (m/z) 332.1621 (M$^+$, 18%, calcd for C$_{19}$H$_{24}$O$_5$: 332.1624), 181.0864 (100%, calcd for $C_{10}H_{13}O_3$: 181.0865), 151.0762 (50%, calcd for $C_9H_{11}O_2$: 151.0759).

EXAMPLE 39

Combretastatin B-4 Permethyl ether

Combretastatin B-4 (20 mg) and the 3'hydroxy-3,4',5-trimethoxy bibenzyl (6.2 mg) were each permethylated employing excess methyl iodide and potassium carbonate in acetone as described above to give identical products: permethyl ether as viscous oils: IR $v_{max}$ 1606, 1594, 1514, 1463, 1428, 1419, 1204, 1151 cm$^{-1}$; $^1$H-NMR (400 MHz) 2.843 (4H, s, ARCH$_2$), 3.763 (6H, s, 2 ×OCH$_3$), 3,843 (3H, s, OCH$_3$), 3.857 (3H, s, OCH$_3$), 6.311 (1H, t, J=2.4 Hz, ArH), 6.338 (2H, d, J=2.4 Hz, ArH), 6.672 (1H, d, J=1.9 Hz, ArH), 6.728 (1H), dd, J=8.2, 1.9 Hz, ArH), 6.792 (1H, d, J=1.9 Hz, ArH); and HREIMS (m/z) 302.1511 (M, 14% calcd for $C_{18}H_2$, $O_4$: 302.1518), 151.0761 (100%, calcd for $C_9H_{11}O_2$: 151.0759).

EXAMPLE 40

3,4-Dibenzyloxy-benzaldehyde

A mixture of 3,4-dihydroxy-benzaldehyde (2.76 g, 20 mmol) in dry acetone (50 ml), potassium carbonate (5.52 g, 40 mmol) and benzylbromide (5 ml, 42 mmol) was heated at reflux for 12 hours. The mixture was cooled to room temperature, potassium carbonate was removed by filtering the solution and the filtrate was concentrated to a powder which was recrystallized from acetone to yield (5.4 g, 81%) ether as prisms, mp 89°–90° (lit. mp 90°) IR $v_{max}$ 1685, 1595, 1483, 1508, 1454, 1434, 1269, 1132, 695, 650 cm$^{-1}$; $^1$H-NMR (90 MHz), 5.21 (2H, s, ArCH$_2$O), 5.26 (2H, s, ArCH$_{20}$), 7.02 (1H, d, J=7.9 Hz), 7.30–7.50 (12H, ArH), 9.81 (1H, s, CHO). Anal. calcd for $C_{21}H_{18}O_3$: C, 79.23; H, 5.70. Found: C, 79.26; H, 5.68.

EXAMPLE 41

3', 4'-Dibenzyloxy-3,4,5-trimethoxy-(Z)-and (E)-stilbene

To a stirred suspension of sodium hydride (0.75, 31.4 mmol) in N,N-dimethylimidazolidinone (10 ml) was added 3,4,5-trimethoxy-benzyl-phosphonium bromide (8.26 g 15.71 mmol) under argon. The aldehyde (4.0 g, 1258 mmol) from Example 40 was added to the deep red solution followed by 2 ml of N,N-dimethylimidazolidinone. Before adding ice (10 g)-water (75 ml) the mixture was stirred overnight. Upon extraction with ethyl acetate (3×100 ml), the organic phase was washed with water (3×75 ml), dried and evaporated to a dark colored mass (9.0 g). The crude product in hexane-ethyl acetate (9:1) was chromatographed on a column of SILICA GEL (200 g) to afford a mixture of E- and Z-isomers (3.70 g, 61% yield). A 1.1 g sample of the mixture was rechromatographed on a column of SILICA GEL and eluted with hexane-ethyl acetate (19:1) to furnish Z-isomer (0.25 g) and E-isomer (0.32 g). The Z-isomer was further purified by preparative TLC (hexane-ethyl acetate, 7:3) to yield 3', 4'-Dibenzyloxy- 3,4,5-trimethoxy-(Z)-stilbene as a chromatographically homogeneous and viscous oil: IR $v_{max}$ 1581, 1509, 1462, 1454, 1412, 1265, 1237, 1128, 1007 cm$^{-1}$; $^1$H-NMR (400 MHz) 3.731 (6H, s, 2×OCH$_3$), 3.856 (3H, s, OCH$_3$), 4.856 (2H, s, ArCH$_2$), 5.121 (2H, s, ARCH$_2$), 6.589 (2H, s, ArH), 6.600 (3H, m, ArH), 6.747 (1H, d, J=8.6 Hz, ArH), 6.758 (1H, brs, ArH), 7,273–7,407 (10H, ArH).

EXAMPLE 42

Combretastatin B-3

A mixture composed of Z- and E-isomers (0.35 g), 5% PD/c (0.10 G) and methanol-ethyl acetate (1:1, 20 ml) was saturated (ambient temperature) with hydrogen at a slightly positive pressure. The reaction mixture was stirred overnight, catalyst was removed by filtration and the crude product was chromatographed (SILICA GEL column). Elution with hexane-ethyl acetate (4:1) yielded combretastatin B-3 (0.20 g, 91%) as a sticky oil which crystallized from ethanol-ether as rods: mp 114°–16° and identical with the natural product.

EXAMPLE 43

Dosage Forms

Several dosage forms were prepared embodying the present invention. They are shown in the following examples in which the notation "active ingredient" signifies one of the disclosed combretastatins, namely, A-1, A-2, A-3, B-1, B-2, B-3 or B-4, their synthetic counterparts and the non-toxic pharmaceutically active derivatives thereof.

COMPOSITION "A"

Hard-Gelatin Capsules

One thousand two-piece hard gelation capsules for oral use, each capsule containing 200 mg of an active ingredient are prepared from the following types and amounts of ingredients:

| | |
|---|---|
| Active ingredient, micronized | 200 gm |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250, 500 mg amounts by substituting 50 gm, 250 gm and 500 gm of a active ingredient for the 200 gm used above.

COMPOSITION "B"

Soft Gelatin Capsules

One-piece soft gelatin capsules for oral use, each containing 200 mg of an active ingredient (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION "C"

Tablets

One thousand tablets, each containing 200 mg of an active ingredient are prepared from the following types and amounts of ingredients:

| | |
|---|---|
| Active ingredient micronized | 200 gm |
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 gm and 100 gm of an active ingredient for the 200 gm used above.

COMPOSITION "D"

Oral Suspension

One thousand ml of an aqueous suspension for oral use, containing in each teaspoonful (5 ml) dose, 50 mg of an active ingredient, is prepared from the following types and amounts of ingredients:

| | |
|---|---|
| Active ingredient micronized | 10 gm |
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml 300 mg of an active ingredient for treating a neoplastic disease, is prepared from the following types and amounts of ingredients:

| | |
|---|---|
| Active ingredient, micronized | 30 gm |
| Polysorbate 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 M) three times a day.

COMPOSITION "F"

Suppository, Rectal and Vaginal

One thousand suppositories, each weighing 2.5 gm and containing 200 mg of an active ingredient are prepared from the following types and amounts of ingredients:

| | |
|---|---|
| Active ingredient, micronized | 15 gm |
| Propylene glycol | 150 gm |
| Polyethylene glycol #4000, q.s. | 2,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating neoplastic disease.

COMPOSITION "G"

Intranasal Suspension

One thousand ml of a sterile aqueous suspension for intranasal instillation, containing in each ml 200 mg of a active ingredient, is prepared from the following types and amounts of ingredients:

| | |
|---|---|
| Active ingredient, micronized | 15 gm |
| Polysorbate 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filed into sterile containers.

The composition so prepared is useful for treating a neoplastic disease, by intranasal instillation of 0.2 to 0.5 ml given one to four times per day.

An active ingredient can also be present, as shown in Compositions H, I, and J in the undiluted pure form for use locally about the cutis, intranasally, pharyngolaryngeally, bronchially, broncholially or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times per day.

COMPOSITION "K"

Hard Gelatin Capsules

One hundred two-piece hard gelatin capsules for oral use, each capsule containing 200 mg of a active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 50, 250 and 500 mg amounts by substituting 50 gm, 250 gm and 500 gm of the active ingredient for the 200 gm used above.

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A substantially pure substance having the structure of either:

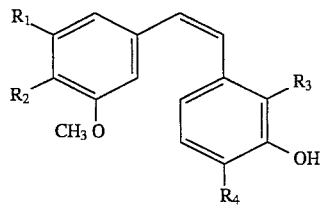

or

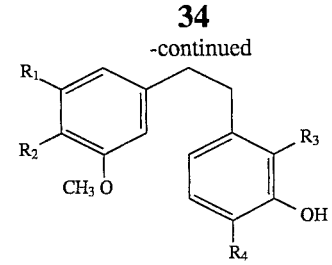

wherein: $R_1$ is OH or $OCH_3$ and $R_2$ is H or $OCH_3$ or $R_1R_2$ is —$OCH_2O$—, $R_3$ is H or OH, and $R_4$ is OH or $OCH_3$, with the proviso that when structure (I) is selected and $R_1$ is $OCH_3$, $R_2$ is $OCH_3$, $R_3$ is OH and $R_4$ is $OCH_3$; and that when structure (I) is selected and $R_1R_2$ is —$OCH_2O$—, $R_3$ is H and $R_4$ is $OCH_3$; and that when structure (I) is selected and $R_1$ is OH, $R_2$ is $OCH_3$, $R_3$ is H and $R_4$ is $OCH_3$; and that when structure (II) is selected and $R_4$ is OH, $R_1$ is $OCH_3$, $R_2$ is H or $OCH_3$ and $R_3$ is H; and that when structure (II) is selected and $R_1=R_2=OCH_3$, $R_3$ is OH and $R_2$ is $OCH_3$; and that when structure (II) is selected and $R_3$ is OH, $R_4$ is $OCH_3$, $R_3$ is H and $R_4$ is $OCH_3$.

2. An antineoplastic substance according to claim 1 denominated combretastatin A-1 and having structural formula I wherein: $R_1$ is $OCH_3$; $R_2$ is $OCH_3$ $R_3$ is OH and $R_4$ is $OCH_3$.

3. An antineoplastic substance according to claim 1 denominated combretastatin A-2 and having structural formula I wherein $R_1$ $R_2$ is —$OCH_2O$—; $R_3$ is H and $R_4$ is $OCH_3$.

4. An antineoplastic substance according to claim 1 denominated combretastatin A-3 and having structural formula I wherein $R_1$ is OH; $R_2$ is $OCH_3$; $R_3$ is H and $R_4$ is $OCH_3$.

5. An antineoplastic substance according to claim 1 denominated combretastatin B-1 and having structural formula II wherein $R_1$ is $OCH_3$; $R_2$ is $OCH_3$; $R_3$ is OH and $R_4$ is $OCH_3$.

6. An antineoplastic substance according to claim 1 denominated combretastatin B-2 and having structural formula II wherein $R_1$ is OH; $R_2$ is $OCH_3$; $R_3$ is H and $R_4$ is $OCH_3$.

7. An antineoplastic substance according to claim 1 having the structural formula II wherein $R_1$ is $OCH_3$; $R_2$ is H or $OCH_3$; $R_3$ is H and $R_4$ is OH.

8. A pharmaceutical preparation comprising a pharmaceutically acceptable carrier and containing as its essential ingredient a synthesized substance having the structure of either:

wherein: $R_1$ is OH or $OCH_3$ and $R_2$ is H or $OCH_3$ or $R_1R_2$ is —$OCH_2O$—, $R_3$ is H or OH, and $R_4$ is OH or $OCH_3$, with the proviso that when structure (I) is selected and $R_1$ is $OCH_3$, $R_2$ is $OCH_3$, $R_3$ is OH and $R_4$ is $OCH_3$; and that when structure (I) is selected and $R_1R_2$ is —$OCH_2O$—, $R_3$ is H and $R_4$ is $OCH_3$; and that when structure (I) is selected and $R_1$ is OH, $R_2$ is $OCH_3$, $R_3$ is H and $R_4$ is $OCH_3$; and that when structure (II) is selected and $R_4$ is OH, $R_1$ is $OCH_3$, $R_2$ is H or $OCH_3$ and $R_2$ is H; and that when structure (II) is selected and $R_1=R_2=OCH_3$, $R_3$ is OH and $R_4$ is $OCH_3$; and that when structure (II) is selected and $R_1$ is OH, $R_2$ is $OCH_3$, $R_3$ is H and $R_4$ is $OCH_3$.

9. A pharmaceutical preparation according to claim 8 in which said substance is denominated combretastatin A-1 and has the structure I wherein: $R_1$ is $OCH_3$; $R_2$ is $OCH_3$; $R_3$ is OH and $R_4$ is $OCH_3$.

10. A pharmaceutical preparation according to claim 8 in which said substance is denominated combretastatin A-2 and has the structure I wherein: $R_1$ $R_2$ is —$OCH_2O$—; $R_3$ is H and $R_4$ is $OCH_3$.

11. A pharmaceutical preparation according to claim 8 in which said substance is denominated combretastatin A-3 and has the structure I wherein: $R_1$ is OH; $R_2$ is $OCH_3$; $R_3$ is H and $R_4$ is $OCH_3$.

12. A pharmaceutical preparation according to claim 8 in which said substance is denominated combretastatin B-1 and has the structure II wherein: $R_1$ is $OCH_3$; $R_2$ is $OCH_3$; $R_3$ is OH and $R_4$ is $OCH_3$.

13. A pharmaceutical preparation according to claim 8 in which said substance is denominated combretastatin B-2 and has the structure II wherein: $R_1$ is OH; $R_2$ is $OCH_3$; $R_3$ is H and $R_4$ is $OCH_3$.

14. A pharmaceutical preparation according to claim 8 in which said substance has the structural formula II wherein: $R_1$ is $OCH_3$; $R_3$ is H; and $R_4$ is OH and is denominated combretastatin B-3 when $R_2$ is $OCH_3$ and is denominated combretastatin B-4 when $R_2$ is H.

* * * * *